(12) United States Patent
Krause et al.

(10) Patent No.: US 11,596,902 B2
(45) Date of Patent: Mar. 7, 2023

(54) IRRADIATED MEMBRANE FOR CELL EXPANSION

(71) Applicant: GAMBRO LUNDIA AB, Lund (SE)

(72) Inventors: Bernd Krause, Rangendingen (DE); Markus Neubauer, Penzberg (DE); Joachim Loercher, Mossingen (DE)

(73) Assignee: GAMBRO LUNDIA AB, Lund (SE)

( * ) Notice: Subject to any disclaimer, the term of this patent is extended or adjusted under 35 U.S.C. 154(b) by 191 days.

(21) Appl. No.: 17/189,515

(22) Filed: Mar. 2, 2021

(65) Prior Publication Data
US 2021/0178333 A1 Jun. 17, 2021

Related U.S. Application Data

(62) Division of application No. 13/120,375, filed as application No. PCT/EP2009/006847 on Sep. 23, 2009, now Pat. No. 10,974,201.

(30) Foreign Application Priority Data

Sep. 25, 2008 (EP) ..................................... 08016834

(51) Int. Cl.
| | |
|---|---|
| C12M 1/12 | (2006.01) |
| B01D 67/00 | (2006.01) |
| C12N 5/00 | (2006.01) |
| C12N 5/0775 | (2010.01) |
| A61L 2/02 | (2006.01) |

(52) U.S. Cl.
CPC .......... B01D 67/009 (2013.01); C12M 25/02 (2013.01); C12N 5/0068 (2013.01); C12N 5/0663 (2013.01); A61L 2/022 (2013.01); C12N 2533/30 (2013.01); C12N 2533/52 (2013.01)

(58) Field of Classification Search
None
See application file for complete search history.

(56) References Cited

U.S. PATENT DOCUMENTS 5,344,701 A * 9/1994 Gagnon ........... G01N 33/54353
428/308.8
2005/0025801 A1 * 2/2005 Richard .................. A61L 31/10
424/422

* cited by examiner

*Primary Examiner* — Erin M. Bowers
(74) *Attorney, Agent, or Firm* — Barnes & Thornburg LLP

(57) ABSTRACT

The invention relates to a membrane which can be used for cultivating adherent or suspension cells, in particular adherent cells, wherein said membrane allows for the adhesion and proliferation of the cells due to the irradiation of the wet or dry membrane with gamma- or beta-rays or an electron beam in a dose of from 12.5 to 175 kGy in the presence of oxygen. The resulting membrane may be used without any pre-treatment with surface-modifying substances. The invention further relates to a method for preparing said irradiated membrane which can be used for the cultivation of cells, in particular adherent cells, and to methods of using such a membrane for the cultivation of cells, in particular adherent cells.

20 Claims, 10 Drawing Sheets

IRRADIATED MEMBRANE FOR CELL EXPANSION

CROSS-REFERENCE TO RELATED APPLICATIONS

This application is a divisional application of U.S. patent application Ser. No. 13/120,375, filed on Mar. 22, 2011, which is the U.S. national phase of PCT/EP2009/06847, filed on Sep. 23, 2009, which claims priority to European Patent Application 08016834.7, filed on Sep. 25, 2008. The disclosures of U.S. patent application Ser. No. 13/120,375, European Patent Application 08016834.7, and PCT/EP2009/06847 are hereby incorporated herein by reference in their entireties.

TECHNICAL FIELD

The invention relates to a membrane which can be used for cultivating adherent or suspension cells, in particular adherent cells, wherein said membrane allows for the adhesion and proliferation of the cells due to the irradiation of the wet or dry membrane with gamma- or beta-rays or an electron beam in a dose of from 12.5 to 175 kGy in the presence of oxygen. The resulting membrane may be used without any pre-treatment with surface-modifying substances. The invention further relates to a method for preparing said irradiated membrane which can be used for the cultivation of cells, in particular adherent cells, and to methods of using such a membrane for the cultivation of cells, in particular adherent cells.

BACKGROUND OF THE INVENTION

The aim of the current invention was the identification of membranes which exhibit growth characteristics substantially similar to tissue culture polystyrene (TCPS) plates which represent today's gold standard for cell expansion using culture flasks or cell stacks. Principal characteristics to be measured were cell expansion rate, re-attachment efficiency of cells onto membranes, and characteristics of cell post-expansion including morphology control, phenotype, and differentiation potential. Such a membrane should be a suitable for being manufactured in various geometries, such as flat sheet or hollow fiber membranes.

The invention particularly relates to membranes which can, for example, be used for culturing, growing, storing and/or expanding adherent cells of various types. In the context of the present invention, the expression "cell culture" or "culturing (of) cells" shall comprise all such uses, i.e. the adherence, maintenance, growth, expansion, differentiation, molecular biological modification (e.g. transfection), and/or storage of cells of different types.

Like most cells in vivo, many cells are adherent cells, or anchorage-dependent cells; that is, they can metabolize and divide only if they are attached to a surface or substrate. Only cells of the circulatory system (e.g., lymphocytes and red blood cells) and other cell types such as hematopoietic stem cells, hepatocytes, CHO cells, etc. grow unattached and suspended in solution in vitro. While many anchorage-dependent cells may grow on glass or synthetic surfaces, these cells often lose their ability to differentiate and respond to hormones. The loss of cellular morphology not only entails a loss of function, but also prevents regenerative power in a longer-term culture system. Longer-term cultivation would however be of great significance, for example, with the use of human cells for tissue culture, and many cells are not available in any quantity. For this reason, such tissue culture dishes are often coated with extracellular matrix components such as collagen or fibronectin. However, the use of xenogenic factors is a clear disadvantage, especially if the cells as such or on a matrix as used for medical treatment of human beings, as it will bring along risks of contamination and may result in adverse reactions in the patient treated.

The failure of cells to grow on such surfaces or keep their abilities is, for example, a major limitation of current tissue culture techniques. Tissue cultures are a potential source of tissues and organs which could be used for transplantation into humans. For example, tissue cultured skin cells could potentially be used in skin grafts. The aim is to develop biological substitutes that can restore and maintain normal function, for example, by the use of acellular matrices, which will depend on the body's ability to regenerate for proper orientation and direction of new tissue growth, or by the use of matrices or membranes with cells adhered thereto (Atala (2006): Recent developments in tissue engineering and regenerative medicine. Curr. Opin. Pediatr. 16, 167-171). Cells can also be used for therapy via injection, either with carriers or alone. In such cases, the cells need to be expanded in culture, attached to a support matrix, and then reimplanted into the host after expansion. Veterinary therapeutic applications are available today and may represent an additional application of membranes for cell cultivation.

The ability to culture cells, especially adherent cells, is important also because they represent biological "factories" capable of producing large quantities of bio products such as growth factors, antibodies and viruses. These products can then be isolated from the cell cultures and used, for example, to treat human diseases.

Additionally, cell cultures are emerging tools for biocompatibility and toxicology studies in the field of pharmaceutical and life science industry.

Finally, tissue cultures usually comprise cells from only one or a few tissues or organs. Consequently, cell cultures provide scientists a system for studying the properties of individual cell types without the complications of working with the entire organism.

A known method for culturing adherent cells involves a hollow fiber membrane bioreactor. In this system, the cells are generally attached to the lumen of a cylindrical hollow fiber membrane. Culture media and oxygen flows through the center of the cylindrical hollow fiber membrane. The molecular weight cut-off of the membrane permits nutrients and oxygen to reach the cells without allowing the cells to escape.

A variety of polymers has been suggested for producing semi-permeable membranes for cell and tissue culture (US 2007/269489). They include polyalginate, polyvinylchloride, polyvinylidene fluoride, polyurethane isocyanate, cellulose acetate, cellulose diacetate, cellulose triacetate, cellulose nitrate, polysulfone, polyethersulfone, polystyrene, polyurethane, polyvinyl alcohol, polyacrylonitrile, polyamide, polymethylmethacrylate, polytetrafluoroethylene, polyethylene oxide and combinations of such polymers. The polymeric support may also consist of polyethylene terephthalate (PET) or polycarbonate. Further materials which were suggested, for example, as scaffolds for transplantable tissue material, are cellulose or macroporous collagen carriers, or biodegradable matrices.

WO 93/00439 A1 describes maintaining a cell culture within a biocompatible, semipermeable membrane in which the cells are stimulated and secrete active factor. The semipermeable membrane used permits the diffusion of the active factor therethrough while excluding detrimental agents present in the external environment from gaining access to the culture. The membrane described has a tubular shape and is said to enable the diffusion of molecules having a molecular weight of up to 150 kDa. Suggested materials for said membrane are acrylic copolymers, polyvinylchloride, polystyrene, polyurethane, polyamide, polymethacrylate, polysulfone, polyacrylate, polyvinylidene fluoride, polyurethaneisocyanate, polyalginate, cellulose acetate, polysulfone, polyvinyl alcohols, polyacrylonitrile, polyethylene oxide, and derivatives and mixtures thereof. The use of any irradiation for preparing such membrane is not described. The membrane does not, as such, have to serve as a matrix for cell adhesion in this disclosure.

WO 90/11820 A2 discloses flat membranes with surfaces usable for cell growth in vitro or as an artificial implant in vivo. The membrane is described as being porous with a pore size in the range of 0.1 to 100 microns and as having a finger-like configuration in an intermediate layer. The membrane comprises a hydrophobic polymer and a hydrophilic polymer. Examples given for the hydrophobic polymer comprise polysulfone, polyamides, polyethersulfone, polyesters, polycarbonates, preferably polyether urethane, and copolymers thereof. The reference does not report whether or not the membrane can be used for adhering and culturing cells. The use of any irradiation technique is not described.

Apart from the problem of identifying membrane compositions which could be used as a matrix for the cultivation of adherent cells, membranes currently known in the art suffer from their inability to sufficiently promote and sustain adherence, expansion, differentiation and extended lifespan without the pre-treatment of said membranes or matrices, or the addition of exogenous factors, such as, for example, fibronectin, laminin or collagen.

For example, Fissell (2006) in *Expert Rev. Med. Devices* 3(2), 155, reviews efforts with regard to developing an artificial kidney based on adhering renal tubule cells to a synthetic polysulfone-based hollow-fiber membrane. In this case the membrane has to be coated with ProNectin-L™ in order to promote attachment of the cells.

U.S. Pat. Nos. 6,150,164 and 6,942,879 both present elaborate ways towards a bioartificial kidney based on renal cells such as, for example, endothelial cells or so-called renal stem cells, which are seeded into hollow fibers. Hollow fiber membranes which are mentioned as being useful are based on cellulose, polyacrylonitrile, polysulfone and other components or copolymers thereof. The internal and external surface of the hollow fiber is pre-coated with suitable extracellular matrix components (EMC) including Type I collagen, Type IV collagen, laminin, Matrigel, proteoglycan, fibronectin and combinations thereof. Only after such treatment the cells can be seeded.

It is a known procedure to submit synthetic membranes, such as polysulfone-based membranes, to gamma-irradiation in order to cross-link certain components of the membrane, such as, for example, PVP, or in order to sterilize the membranes. The radiation dose will generally be in the range of 10 to 50 kGy, preferably in the range of 20 to 35 kGy (see, for example, U.S. Pat. No. 6,960,297 B2 or U.S. Pat. No. 6,103,117). Higher doses are usually avoided in order to minimize degradation of the membrane. In addition, said known processes are generally designed in a way to omit the presence of oxygen for the same reasons, i.e. the formation of and membrane degradation by aggressive oxygen derivatives, such as oxygen radicals or $H_2O_2$. The sterilization by gamma-irradiation is generally performed under aqueous conditions, i.e. with wet membranes, wherein the solution is degassed to remove oxygen. In case dry conditions are used, oxygen is also removed from the system, by using an inert gas atmosphere, oxygen scavengers etc.

Further, it is the clear objective of said membranes and processes of the prior art to avoid or minimize the adhesion of cells to the membrane which will generally be used in dialysis treatments. This is contrary to the objective of the present invention which is focused on providing a surface which is favorable for the adhesion and growth of cells. Accordingly, the methods described in the prior art are designed to provide membranes which will not be useful for the purpose of the present invention, i.e. the cultivation of cells.

EP 1 795 254 A1 describes the formation of a polysulfone-based membrane, wherein the membrane is exposed to a radioactive ray, such as gamma-ray, under conditions where the oxygen concentration in the ambient atmosphere around the membrane is from 0.001 to 0.1% or lower and the moisture content of the membrane is from 0.2 to 7 wt.-%, related to the weight thereof. It is stated in this reference that higher oxygen concentrations, especially the use of atmospheric air, will result in excited oxygen radicals which will break the main chains of the polymers and decompose them and that therefore it is desirable to have an atmosphere of inert gas, preferably also in the presence of an oxygen scavenger. As it is difficult to absolutely exclude any oxygen, the above-mentioned limit is suggested as highest oxygen level. EP 1 795 254 A1 further notes that the radiation dose should be 1 to 50 kGy, or better 10 to 30 kGy, in case of using gamma-rays. Lower doses will result in insufficient sterilization while higher doses will disintegrate the components of the membrane. The reference does not contemplate the use of the membranes for cell culture.

JP 2003/245526 also describes a method for irradiating a hollow fiber membrane without using wet (water filled) fibers. In this method, the moisture content is adjusted to at least 4% with respect to the weight of the hollow fiber membranes. The concentration of oxygen in the hollow fiber membrane module is set to 0.1 to 3.6%.

US 2006/191844 describes the treatment of a membrane module by charging it with a degassed aqueous RO solution followed by sealing, wherein the module is then exposed to 10 to 60 kGy of gamma-rays. When the dosage of gamma-rays is too high, the hydrophobic polymer, the hydrophilic polymer and/or the housing may be disintegrated and deteriorated. Thus, the dosage of gamma-rays is disclosed to be preferably 50 kGy or less, particularly 30 kGy or less. When non-degassed water is used, the oxygen dissolved in the water oxidizes and deteriorates the components of the membrane.

WO 2006/135966 A1 discloses a method for cross-linking hydrophilic components of a membrane, for example PVP, using gamma-radiation, optionally combined with a chemical solution treatment process. The dosage used is from 1 to 100 kGy, preferably 10 to 50 kGy. The irradiation is said to be applicable to dry and wet membranes. However, the examples given use wet membranes and a dosage not exceeding 35 kGy. The use of membranes prepared according to his reference for culturing cells is not mentioned.

EP 1 439 212 A1 also describes the irradiation of a polysulfone and PVP based membrane with gamma-rays. Again, the membrane is irradiated in the wet state, wherein the membrane should contain at least 1 wt.-% or more water or be immersed in water, and doses are not to exceed 50 kGy in order to avoid any degradation of the membrane. It is taught that the irradiation will reduce the adhesion of platelets to the membrane surface, which contrasts to the goal of the present invention, i.e. the adhesion of cells to the membrane surface.

JP 2004/305840 describes a hollow fiber membrane composed of a hydrophobic polymer and a hydrophilic polymer which is sterilized by irradiation with gamma-rays after spinning. Irradiation is performed in a dried and low temperature deoxygenated hermetically closed state. It is important to note that again the exclusion of oxygen is crucial.

SUMMARY OF THE INVENTION

In the present invention, membranes are disclosed which are treated, after preparation, with beta- or gamma-rays or an electron beam at a dose of from 12.5 to 175 kGy in the presence of oxygen. During irradiation, the membrane can be in the dry or wet state, and may be covered by air, water, or aqueous solutions, respectively. The present invention is also directed to a method of preparing such a membrane. The present invention is also directed to methods of using the membrane for promoting cell attachment and for the cultivation of cells, in particular adherent cells, without the need to pre-treat or pre-coat the membranes with any extracellular matrix components. Preferred membranes in the context of the present invention are polysulfone-based, polyethersulfone-based or poly(aryl)ethersulfone-based synthetic membranes, comprising, in addition, PVP and optionally low amounts of further polymers, such as, for example, polyamide or polyurethane.

DETAILED DESCRIPTION OF THE INVENTION

Figure 1:
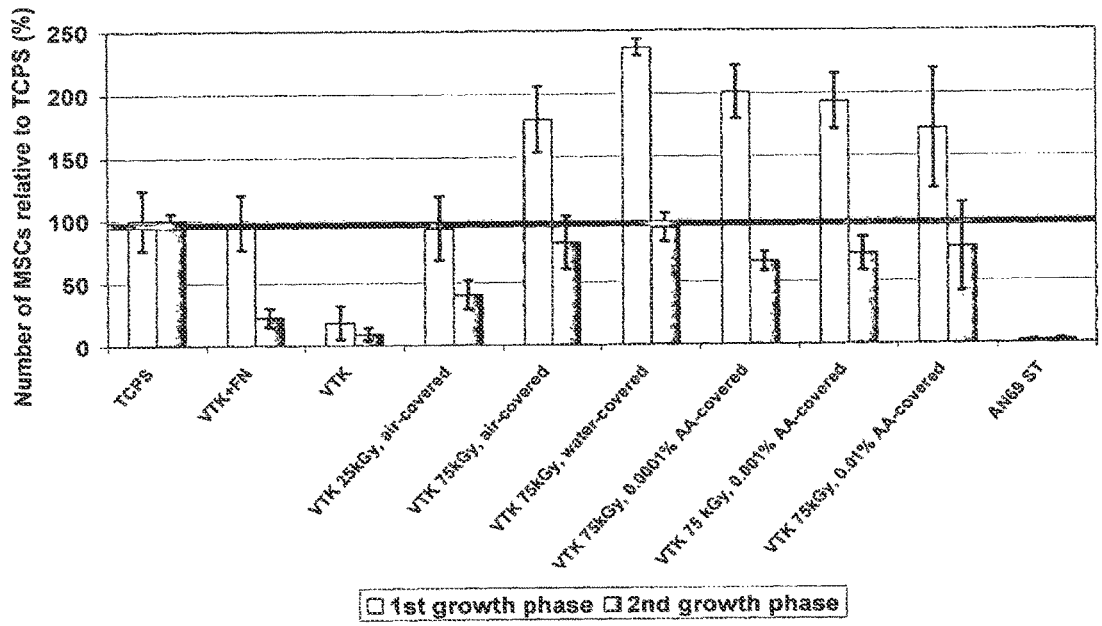
FIG. 1 shows the number of MSC grown from unprocessed bone marrow on various membrane types relative to the number of MSC grown on standard TCPS after the first (14 days) and second (7 days) growth phase in [%] (Experiment 1). The horizontal line indicates TCPS level. For the abbreviations used see Table I.

An object of the present invention is a polymer membrane which has been subjected, either in a dry or wet state, to beta- or gamma-ray or electron beam irradiation at a dose of from 12.5 to 175 kGy in the presence of oxygen. The membrane, during irradiation, may be surrounded by air, wherein oxygen is present during irradiation in a concentration of from 4 to 100 vol.-%, e.g. 5 to 30 vol.-% or 15 to 25 vol.-%, or by water or an aqueous solution comprising low amounts of additives.

The polymer membrane comprises hydrophobic or hydrophilic polymers or both. In one embodiment, the membrane comprises a blend of at least one hydrophilic polymer and at least one hydrophobic polymer. In another embodiment, the membrane comprises hydrophilic copolymers. In yet another embodiment, the membrane comprises hydrophilic copolymers and hydrophobic polymers. In another embodiment, the membrane comprises hydrophilic homopolymers. In a further embodiment, the membrane comprises hydrophilic homopolymers and hydrophobic polymers.

In one embodiment of the invention, the polymer solution used to prepare the membrane comprises hydrophobic and hydrophilic polymers in amounts such that the fraction of hydrophobic polymer in the polymer solution is between 5 and 20% by weight and the fraction of the hydrophilic polymer is between 2 and 13% by weight.

In a particular embodiment, the membrane comprises a first hydrophobic polymer component, a second hydrophilic polymer component, and, optionally, a third hydrophobic polymer component.

Said first hydrophobic polymer is preferably chosen from the group consisting of polyamide (PA), polyaramide (PAA), poly(aryl) ethersulfone (PAES), polyethersulfone (PES), polysulfone (PSU), polyarylsulfone (PASU), polycarbonate (PC), polyether, polyurethane (PUR), polyetherimide and copolymers of said polymers. Said second hydrophilic polymer is preferably chosen from the group consisting of polyvinylpyrrolidone (PVP), polyethylene glycol (PEG), polyglycol monoester, water soluble cellulosic derivates, polysorbate and polyethyleneoxide-polypropyleneoxide copolymers. Said third hydrophobic polymer is preferably chosen from the group consisting of polyamide (PA), polyaramide (PAA), poly(aryl)ethersulfone (PAES), polyethersulfone (PES), polysulfone (PSU), polyarylsulfone (PASU), polycarbonate (PC), polyether, polyurethane (PUR), polyetherimide and copolymers of said polymers. The membranes can be prepared in the form of flat sheet or hollow fiber membranes.

In one aspect of the present invention, the membrane can be used for cell attachment or adherence, cell growth and expansion or storage of cells without the need to pre-treat or pre-coat the membrane with EMC. Advantages of using a membrane without any such EMC for cell cultivation are, for example, lower cost in terms of time savings and less process steps, a significantly reduced risk of contamination brought along with the EMC (GMP-compliance) or the higher number of process steps needed for coating a membrane and significantly better defined materials and protocols for cell production.

It is of course possible to additionally pre-treat or pre-coat the membrane of the present invention with one or more EMC which are generally known in the art. Especially for applications which are not intended for expanding or growing cells or tissues for re-implantation into the host, such pre-treatment may further improve the performance of the membrane in terms of adhesion or proliferation. However, it is always preferable to use the membrane of the invention without any coating with EMC.

In a further aspect of the present invention, the performance in culturing cells can be significantly improved by preparing a hollow fiber membrane of the invention, and by using said hollow fiber membrane or a bundle thereof in a continuous culture process as an alternative to plate culture techniques. Besides a continuous process, the hollow fiber membrane can be used in a static or semi-continuous process.

The membrane of the invention can be prepared in ways that confer the specific adhesive properties to the whole of the membrane, i.e., in case of a hollow fiber membrane for continuous applications, to the outside and inside of the hollow fiber membrane.

In a further aspect of the present invention, the membrane also provides a system for cellular co-cultivation of two or more different cell types.

A further aspect of the present invention is that the membrane very well promotes the formation of an optimal cell monolayer in terms of differentiation and integrity without the need to pre-coat the membrane surface with any EMC. The membrane of the invention provides for the retention of typical cell morphology, a monolayer is readily formed, and tight junctions can be created. In the context of the present invention, a monolayer refers to a layer of cells in which no cell is growing on top of another, but all are growing side by side and are in many cases touching each other on the same growth surface, even though this is not necessary for all potential applications of the membrane.

The membrane of the invention can thus be advantageously used, for example,
(a) in tissue culture technology, i.e. for establishing bio-artificial implants, such as bioartificial kidneys or livers (see also Atala (2006);
(b) for cultivating adherent cells, such as, for example, MSC, smooth muscle cells, skin cells, nerve cells, neuroglia or endothelial cells in general, or suspension cells, such as hematopoietic stem cells, cord blood cells, neural stem cells, etc. for use in medical therapies via injection of cells, which need to be expanded in vitro before being re-implanted into the host;

(c) for expanding and providing cells which serve as producers of bio products such as growth factors, recombinant proteins, cytokines or antibodies, such as monoclonal antibodies;

(d) for preparing cultures of adherent cells, preferably cell monolayer cultures, for studying specific cell types or for studying the influence of any drugs on cells (screening procedures), such as, for example, anti-cancer agents, anti-fungals, antibiotics, antivirals (including anti-HIV) and anti-parasitic drugs; (e) or any other application which is based on or requires the culturing expansion or storage of adherent or suspension cells in an in vitro system.

The membrane of the invention can have any suitable geometry according to the needs of the intended use, i.e. it can be a flat sheet, a hollow fiber or a bundle of hollow fibers, or can be shaped to form chambers or other geometries desired. The core unit for cell expansion preferably is a hollow fiber-based membrane system allowing sufficient exchange of $O_2$ and $CO_2$, supply of nutrients and removal of waste products. The surface of the membrane is designed to enable adhesion and proliferation of cells having the desired properties through specific surface characteristics. The advantages of the cultivation of cells inside of hollow fibers is based on the advantageous surface to volume ratio which results in the minimization of medium consumption in the cultivation process, the minimization of space requirements and the minimization of labor as compared to conventional flask or cell stack culture methods. Another advantage of the hollow fiber structure is uniform controlled flow paths.

The membrane of the invention can be used in various kinds of cell expansion or cell culturing devices or systems, such as described, for example, in US 2003/0203478 A1, U.S. Pat. No. 6,150,164 or 6,942,879.

The membrane of the present invention can be advantageously used for culturing adherent cells in general. Adherent cells are defined, in the context of the present invention, as cells attaching to a substrate which are to be maintained, expanded, differentiated, stored, etc. The membrane of the invention will be used for culturing, for example, stem cells, including embryonic and adult stem cells, especially mesenchymal stem cells (MSC), fibroblasts, epithelial cells, hepatocytes, endothelial cells, muscle cells, chondrocytes, etc.

In a first aspect of the invention, membranes of the invention are prepared from a polymer mixture comprising hydrophobic and hydrophilic polymers in amounts such that the fraction of hydrophobic polymer in the polymer solution used to prepare the membrane is from 5 to 20% by weight and the fraction of the hydrophilic polymer is from 2 to 13% by weight. Said at least one hydrophobic polymer is preferably chosen from the group consisting of polyamide (PA), polyaramide (PAA), polyarylethersulfone (PAES), polyethersulfone (PES), polysulfone (PSU), polyarylsulfone (PASU), polycarbonate (PC), polyether, polyurethane (PUR), polyetherimide and copolymers of said polymers, preferably polyethersulfone or a mixture of polyarylethersulfone and polyamide. Said at least one hydrophilic polymer is preferably chosen from the group consisting of polyvinylpyrrolidone (PVP), polyethylene glycol (PEG), polyglycolmonoester, water soluble cellulosic derivates, polysorbate and polyethylene-polypropylene oxide copolymers, preferably polyvinylpyrrolidone.

A membrane which may be preferably used in the context of the present invention comprises, in the polymer solution for preparing the membrane, from 11 to 19 wt.-% of a first polymer selected from the group consisting of polysulfone (PS), polyethersulfone (PES) and polyarylethersulfone (PAES), from 0.5 to 13 wt.-% of a second polymer such as polyvinylpyrrolidone (PVP), from 0 wt.-% to 5 wt.-%, preferably from 0.001 to 5 wt.-% of a polyamide (PA), from 0 to 7 wt.-% of water and, the balance to 100 wt.-%, of a solvent selected from the group consisting of N-methyl-2-pyrrolidone (NMP), which is preferred, N-ethyl-2-pyrrolidone (NEP), N-octyl-2-pyrollidone (NOP), dimethyl acetamide, dimethyl formamide (DMF), dimethyl sulfoxide (DMSO) and gamma-butyrolactone (GBL).

Preferably, the polyvinylpyrrolidone (PVP) in the polymer solution consists of a blend of at least two homopolymers of polyvinylpyrrolidone wherein one of the homopolymers of polyvinylpyrrolidone (=low molecular weight PVP) has an average relative molecular weight of from about 10,000 g/mol to 100,000 g/mol, preferably about 30,000 g/mol to 70,000 g/mol, and another one of the homopolymers of polyvinylpyrrolidone (=high molecular weight PVP) has an average relative molecular weight of from about 500,000 g/mol to 2,000,000 g/mol, preferably about 800,000 g/mol to 2,000,000 g/mol. Examples of such PVP homopolymers are PVP K85, a high molecular weight PVP having a molecular weight of about 825,000 Da, and PVP K30, a low molecular weight PVP having a molecular weight of about 66,800 Da. In a preferred embodiment of the present invention, the polymer solution for preparing the membrane comprises from 0.5 to 5 wt.-% of a high molecular weight PVP and from 1 to 8 wt.-% of a low molecular weight PVP.

Methods for preparing such membranes are described in detail, for example, in U.S. Pat. Nos. 4,935,141, 5,891,338 and EP 1 578 521 A1, all of which are incorporated herein by reference. Examples for this type of membrane, which can be effectively treated according to the present invention, are Gambro Polyflux™ membranes (polyarylethersulfone/PVP/polyamide), which are currently used in commercial products, such as, for example, Polyflux™ L and H series; Arylane™ membranes (poly(aryl)ethersulfone/PVP); or DIAPES™ or PUREMA™ membranes (poly(aryl)ethersulfone/PVP) or other commercial dialysis membranes based on blends of hydrophilic and hydrophobic polymers, e.g. blends comprising PVP and PES or polysulfone.

In a second aspect of the present invention, the polymer solution used to prepare the membrane of the invention comprises from 12 to 15 wt.-% of polyethersulfone or polysulfone as hydrophobic polymer and from 5 to 10 wt.-% of PVP, wherein said PVP consists of a low and a high molecular PVP component. The total PVP contained in the spinning solution consists of from 22 to 34 wt.-%, preferably of from 25 to 30 wt.-%, of a high molecular weight (>100 kDa) component and from 66 to 78 wt.-%, preferably from 70 to 75 wt.-% of a low molecular weight (<=100 kDa) component. Examples for high and low molecular weight PVP are, for example, PVP K85/K90 and PVP K30, respectively. The polymer solution used in the process of the present invention preferably further comprises from 66 to 86 wt.-% of solvent and from 1 to 5 wt.-% suitable additives. Suitable additives are, for example, water, glycerol and/or other alcohols. Water is especially preferred and, when used, is present in the spinning solution in an amount of from 1 to 8 wt.-%, preferably from 2 to 5 wt.-%. The solvent used in the process of the present invention preferably is chosen from N-methylpyrrolidone (NMP), dimethyl acetamide (DMAC), dimethyl sulfoxide (DMSO), dimethyl formamide (DMF), butyrolactone and mixtures of said solvents. NMP is especially preferred. The center fluid or bore liquid which is used for preparing the membrane comprises at least one of the above-mentioned solvents and a precipitation medium chosen from water, glycerol and other alcohols. Most preferably, the center fluid consists of 45 to 70 wt.-% precipitation medium and 30 to 55 wt.-% of solvent. Preferably, the center fluid consists of 51 to 57 wt.-% of water and 43 to 49 wt.-% of NMP.

Methods for preparing such membranes are disclosed in detail in European Patent Application No. 08008229, expressly incorporated herein by reference. Examples for this type of membrane, which can be treated effectively according to the present invention, are, for example, the Gambro Revaclear™ membrane and derivatives thereof. It is also possible to use, in the context of the present invention, membranes which are currently used in commercial products, such as, for example, the Fresenius FX™-class membranes (Helixone™ membranes) or Optiflux™ type membranes) or other commercial dialysis membranes based on blends of hydrophilic and hydrophobic polymers, e.g. blends comprising PVP and PES or polysulfone.

In a third aspect of the present invention, the polymer solution used to prepare the membrane of the invention comprises from 11 to 19 wt.-% of a first polymer selected from the group consisting of polysulfone (PS), polyethersulfone (PES) and polyarylethersulfone (PAES), from 0.5 to 13 wt.-% of a second polymer such as polyvinylpyrrolidone (PVP), from 0.001 to 20 wt.-% of a polyurethane (PU), from 0 to 7 wt.-% water and a solvent selected from the group consisting of N-methyl-2-pyrrolidone (NMP), N-ethyl-2-pyrrolidone (NEP), N-octyl-2-pyrollidone (NOP), dimethyl acetamide, dimethyl formamide (DMF), dimethyl sulfoxide (DMSO) and gamma-butyrolactone (GBL), adding up to 100 wt.-%. Said first polymer is preferably present in the polymer solution in an amount of from 13 to 14 wt.-%, especially preferably in an amount of from 13.6 to 14 wt.-%. Polyethersulfone (PES) and polyarylethersulfone (PAES) are preferably used for preparing a membrane of the invention. Preferably, the polyvinylpyrrolidone (PVP) in the polymer solution consists of a blend of at least two homopolymers of polyvinylpyrrolidone wherein one of the homopolymers of polyvinylpyrrolidone (=low molecular weight PVP) has an average relative molecular weight of about 10,000 g/mol to 100,000 g/mol, preferably about 30,000 g/mol to 70,000 g/mol, and another one of the homopolymers of polyvinylpyrrolidone (=high molecular weight PVP) has an average relative molecular weight of about 500,000 g/mol to 2,000,000 g/mol, preferably about 800,000 g/mol to 2,000,000 g/mol. Examples for such PVP homopolymers are PVP K85, a high molecular weight PVP having a molecular weight of about 825,000 Da, and PVP K30, a low molecular weight PVP having a molecular weight of about 66,800 Da. In a preferred embodiment of the present invention, the polymer solution for preparing the membrane comprises from 0.5 to 5 wt.-% of a high molecular weight PVP and from 1 to 8 wt.-% of a low molecular weight PVP. The water content of the spinning solution preferably is from 1 to 5 wt.-%, more preferably about 3 wt.-%. Various solvents can be used for preparing a membrane of the invention, such as N-methyl-2-pyrrolidone (NMP), N-ethyl-2-pyrrolidone (NEP), N-octyl-2-pyrrolidone (NOP), dimethyl acetamide, dimethyl formamide (DMF), dimethyl sulfoxide (DMSO) or gamma-butyrolactone (GBL) and mixtures thereof. The solvent will be present in an amount to add up to 100 wt.-% of the polymer solution. The content of the solvent in the polymer solution preferably is from 60 to 80 wt.-%, more preferably from 67 to 76.4 wt.-%.

The membranes of the invention can be prepared, for example, in flat sheet or hollow fiber geometry.

In one embodiment, the membranes of the invention have an asymmetric structure. In the case of hollow fibers, there is a thin separation layer on the inner side of the fibers. The structure or morphology of the membrane of the invention may otherwise vary without significant impact on its performance regarding cell adhesion and proliferation. The membranes may have, for example, a 3-layer structure or a sponge-like structure or a foam-like structure. In one embodiment, the membrane of the invention is further characterized by the smoothness or low roughness of the cell adhesion side.

In one embodiment, the hydraulic permeability of a membrane of the invention may vary from about $0.1 \cdot 10^{-4}$ cm$^3$ to $200 \cdot 10^{-4}$ cm$^3$/(cm$^2$ bar sec), e.g. $0.1 \cdot 10^{-4}$ cm$^3$ to $10 \cdot 10^{-4}$ cm$^3$/(cm$^2$ bar sec), or even $0.1 \cdot 10^{-4}$ cm$^3$ to $5 \cdot 10^{-4}$ cm$^3$/(cm$^2$ bar sec). In order to achieve such hydraulic permeability without getting defects in the membrane structure, the viscosity of the polymer solution usually will be in the range of from 2,500 centipoise (cP) to 200,000 cP, or even from 10,900 cP to 25,600 cP for hollow fiber production. For flat sheet membrane production the viscosity generally will be in the range of from 2,500 cP to 500,000 cP, or even from 4,500 cP to 415,000 cP.

For preparing the membranes of the invention, the polymers are dissolved in the solvent at constant temperature and pressure. Degassing of the polymer solution is performed in a drying oven creating a vacuum (approximately 100 mbar). The temperature of the polymer solution may vary over a relatively broad range. It is advantageous to choose a temperature in the range of from ambient temperature to 60° C.

For preparing a flat sheet membrane, the final polymer solution is cast as an uniform film onto a smooth surface such as a glass slide which acts as a supporting area, by utilizing a special coating knife. The velocity of casting the polymer film can vary over a relatively broad range. A velocity between 10 and 20 mm/s may be appropriate. In an exemplary lab-scale process, the polymer solution first is applied steady-going onto the glass slide using a syringe. It is important to work bubble free. The coating knife with a defined gap height is driven with constant velocity, creating a uniform polymer film. For a good thickness distribution, a coating knife having a uniform gap is advisable.

In one embodiment of the invention, the precipitation bath comprises H$_2$O in an amount of from 30 to 100 wt. %, preferably in an amount of from 56 to 66 wt.-%, and a solvent, such as NMP, in an amount of from 0 to 70 wt.-%, preferably from 34 to 44 wt.-%. The temperature of the precipitation bath can be varied over a relatively broad range. It may be advantageous to apply a temperature between 0° C. and 80° C., or between 30° C. and 50° C. The precipitation time can also be varied. As an example, the precipitation time may be about five minutes. The precipitation bath preferably consists of H$_2$O and a solvent. The bath preferably comprises H$_2$O in amount of from 30 wt.-% to 100 wt.-%, and a solvent selected from N-methyl-2-pyrrolidone (NMP), N-ethyl-2-pyrrolidone (NEP), N-octyl-2-pyrollidone (NOP), dimethyl acetamide, dimethyl formamide (DMF), dimethyl sulfoxide (DMSO) or gamma-butyrolactone (GBL) and mixtures thereof in an amount of from 70 wt.-% to 0 wt.-%. In one embodiment of the invention, the precipitation bath comprises H$_2$O in an amount of from 56 to 66 wt.-%, and a solvent in an amount of from 34 to 44 wt.-%. NMP is an especially suitable solvent in the context of the present invention.

The precipitated membrane is then stored in a non-solvent until the membrane is cut. After cutting, the membrane is washed, dried and sterilized.

The thickness of a flat sheet membrane of the invention may vary between 15 µm and 200 µm. A thickness of 35 µm to 50 µm may be especially advantageous for most applications.

The membranes of the invention can also be prepared in hollow fiber geometry. For preparing such hollow fiber membranes, the solution is pumped through a spinning die and the liquid hollow fiber is formed. The solvent concentration in the center results in an open structure at the inner side of the membrane. The smallest pores are directly at the inner side of the membrane. When in use, the selective layer at the inside is in direct contact with cell medium.

In one embodiment, the precipitation bath consists of water. The temperature of the precipitation bath may be varied over a broad range, but ambient temperature up to about 40° C. is advantageously used in the process. The distance between the die and the precipitation bath is in the range of from 0 to 100 cm, e.g. from 50 to 100 cm. The die (spinneret) temperature can also be varied. Temperatures between 20 and 80° C. can be used. It may be advantageous to apply temperatures between 40 and 55° C. The spinning speed may be chosen to be in the range of from 5 to 80 m/min, e.g. from 11 to 40 m/min.

The dimensions of a hollow fiber membrane of the invention may be varied depending on the intended use of the membrane. The inner diameter generally is in the range of from 50 to 2,000 µm. For many applications, an inner diameter of from 100 to 950 µm may be advantageous. The wall thickness generally is in the range of from 25 to 55 µm.

The resulting Lp for a membrane of the invention is in the range of from $0.1 \cdot 10^{-4}$ to $200 \cdot 10^{-4}$ cm$^3$/(cm$^2 \cdot$bar·s), e.g. from $0.1 \cdot 10^{-4}$ to $10 \cdot 10^{-4}$ cm$^3$/(cm$^2 \cdot$bar·s), or even from $0.1 \cdot 10^{-4}$ to $5 \cdot 10^{-4}$ cm$^3$/(cm$^2 \cdot$bar·s). In another embodiment of the invention, the Lp of the membranes is in the range of from $2 \cdot 10^{-4}$ to $18 \cdot 10^{-4}$ cm$^3$/(cm$^2 \cdot$bar·s). In still another embodiment of the invention, the Lp of the membranes in the range of from $5 \cdot 10^{-4}$ to $15 \cdot 10^{-4}$ cm$^3$/(cm$^2 \cdot$bar·s). That is, membranes which are to be used for cell culture can be so-called low flux membranes.

There are two ways for producing membranes of the invention which may be referred to as "wet" and "dry". In case "wet" membranes are prepared, the membranes have to be dried separately in a tube or oven after they have been prepared. To this end, bundles of fibers (for example, from 30 to 15,000 fibers) are placed in a plastic or metal container. Hot air is passed through this container to dry the membranes. The second way is the so-called "online drying" which is an efficient way to directly prepare dry hollow fibers on a spinning machine. Both procedures are applicable to arrive at membranes which may be treated and used according to the invention.

According to the invention, membranes as described before are treated by covering them with air or water or aqueous solutions containing suitable additives, such as, for example, acrylic acid, allylamine or acrylamide in concentrations of from 0.00001 wt.-% to 5 wt.-%, e.g. from 0.0001 to 0.01 wt.-%, and subjected to gamma, beta or electron beam irradiation in the presence of oxygen.

To arrive at membranes which may serve for cell culture purposes, the membranes can be placed in an irradiation chamber and subjected to gamma, beta, or electron beam irradiation, in particular gamma-ray irradiation, using radiation doses of from 12.5 to 175 kGy, with a preference for doses of from 70 to 175 kGy. In another aspect of the invention, the doses used are from 25 to 125 kGy. In yet another aspect of the present invention, doses of from 50 to 175 kGy are used. In yet another aspect of the present invention, doses of from 50 to 125 kGy are used. In yet another aspect of the present invention, doses of from 70 to 100 kGy are used.

Gamma-ray irradiation can be performed, for example, by using a Co-60 source. Electron beam irradiation may be performed by using an electron beam accelerator. Beta-ray irradiation can be performed using a beta radiation source, e.g. Sr-90 or Ru-106.

In one embodiment of the present invention, the membrane is subjected to irradiation under dry conditions, i.e. the membrane is covered with or surrounded by air. The expression "dry", in the context of the present invention, does not exclude that water is present within the porous structure of the membrane, i.e. it is intended to encompass the range from complete absence of water to a condition in which the complete porous structure of the membrane wall is filled with water.

In contrast to the known gamma-ray irradiation of membranes which is done, for example, in order to sterilize the membrane or cross-link certain components of the membrane, such as, for example, PVP, the presence of oxygen during irradiation is crucial for obtaining membranes suitable for cell culture purposes. The surrounding air during irradiation, in one aspect of the present invention, may be unmodified air, roughly containing (by molar content/volume) 78.08% nitrogen, 20.95% oxygen, 0.93% argon, 0.038% carbon dioxide, trace amounts of other gases, and a variable amount of water vapor. In another aspect of the present invention, the oxygen content of the surrounding air may be increased, e.g. by additionally introducing oxygen gas into the system. The oxygen concentration may be increased up to a limit of about 100%, e.g. up to 30%. In yet another aspect of the present invention, the oxygen concentration may be lowered down to a limit of about 4%. Oxygen concentrations of from 4% to 100%, e.g. from 4 to 30% (by molar content/volume) may generally be used to achieve the desired results. It may be advantageous to use an oxygen concentration of from 5% to 25%, or even from 15% to 22%.

In another embodiment of the present invention, the membranes are subjected to irradiation in the wet state, or, in other words, under aqueous conditions. The expressions "wet" and "aqueous conditions", in the context of the present invention, refer to the presence of water during the irradiation process, i.e. the membranes may be covered by or immersed in water. In one embodiment of the present invention, RO water is used.

In another embodiment of the present invention, additives may be admixed with the water in low quantities. Such additives may improve the performance of the irradiated membranes for cell culture purposes in general or for specific cell types by introducing functional groups to the membrane surface. Examples for such additives are vinyl group containing monomers having amino, carboxyl or carboxamide functionalities, e.g. acrylic acid, allylamine or acrylamide. In one particular embodiment, acrylic acid is used.

In another particular embodiment, allylamine is used. The additives may be present in the aqueous solution in concentrations of from 0.00001 wt.-% to 5 wt.-%. It may be advantageous to use concentrations of from 0.0001 wt.-% to 1 wt.-%, or from 0.0001 wt.-% to 0.1 wt.-%. Low concentrations of an additive, such as 0.0001 wt.-% to 0.01 wt.-% may prove to be especially effective.

It may be advantageous to use higher radiation doses for the irradiation of membranes in the wet state, such as doses of from 70 to 175 kGy.

The time needed for arriving at the chosen dose may vary over a relatively broad range. As an example, with a Co-60 source, about 6 to 7 hours may be needed for a 25 kGy dose, and about 17 to 20 hours for a 75 kGy dose, i.e. the irradiation time is tripled. The time needed will depend on the source as such and its strength at the time of irradiation and needs to be adjusted.

The temperature may also be varied over a broad range and will also depend on the material of the housing for the membrane, i.e. if the housing is made from metal or a synthetic material. In general, the temperature will be in the range of from 0° C. to 41° C. In most cases, it will be convenient to use room temperature.

In another embodiment of the present invention, the membranes will be subjected to drying, preferably online-drying, followed by steam sterilization, before they are irradiated, in order to retain the desired low-flux characteristics. A further sterilization with EtO (ethylene oxide), if so desired or needed in the preparation process, may be added without negative influence on the efficacy of the membranes of the invention regarding their use for cell culture purposes. Methods for steam-sterilizing or EtO sterilizing membranes are well known in the art.

The irradiated membranes may then be used directly for culturing cells of different types, preferably adherent cells. The membranes of the invention exhibit growth characteristics substantially similar or superior to tissue culture polystyrene (TCPS) plates which represent today's gold standard for cell expansion using culture flasks or cell stacks.

The membranes of the invention show cell expansion rates, re-attachment efficiency of cells onto membranes, and characteristics of the cells' post expansion including morphology control similar or superior to tissue culture polystyrene (TCPS), as shown in tests performed with mesenchymal stem cells (MSC), fibroblasts, epithelial cells and hepatocytes.

A further aspect of the invention is a cell culturing device comprising a membrane of the invention. Examples of cell expansion or cell culturing devices or systems which can be modified to comprise the membrane of the invention are disclosed in US 2003/0203478 A1, U.S. Pat. No. 6,150,164, or U.S. Pat. No. 6,942,879, all incorporated herein by reference. The device can comprise a stack of flat sheet membranes of the invention or a bundle of hollow fiber membranes of the invention.

In one embodiment of the device, the membrane forms an interface between two fluid compartments of the device. The device can be similar in construction to commercially available filtration devices used, for example, in hemodialysis or hemofiltration.

An exemplary device comprises two compartments separated by a semipermeable membrane mounted in a casing, a first internal compartment fitted with two accesses and a second external compartment comprising one or two accesses, both compartments being also separated by a potting compound, based on an appropriate adhesive compound, intended for forming, as applicable, (i) a cylindrical partition separating both compartments of said device containing a semipermeable membrane of the hollow fiber bundle type as defined above or (ii) a tight seal in said device including a semipermeable membrane of the sheet membrane type as defined above.

Another exemplary device comprises a plurality of hollow fiber membranes, contained within an outer shell, and configured so that fluid within a space external to the hollow fibers (i.e., an extracapillary compartment) is segregated from fluid passing through the hollow fibers and their corresponding orifices. Additionally, the device includes two manifold end chambers within the outer shell on opposite ends of the device. Each of the two mouths of a hollow fiber connects to a different end chamber. The end chambers and the extracapillary compartment are separated by the semipermeable membranes of the hollow fibers. The composition within the extracapillary compartment can be controlled, to a certain extent, by the molecular weight cutoff, or pore size, of the membranes of the hollow fibers.

In one mode of operating the device, cells are grown in the extracapillary compartment while a nutrient medium is passed through the hollow fibers. Medium may be passed through the extracapillary or intracapillary compartment. In another mode of operating the device, cells are grown in the intracapillary space (i.e. lumen) of the hollow fibers while a nutrient medium is passed through the extracapillary and/or intracapillary compartment. The semipermeable nature of the hollow fibers allows nutrients, gas and cell waste products to pass through the walls of the hollow fibers while blocking cells from doing the same.

Shell-and-tube type bioreactors provide several advantages. For adherent cells, the use of several hollow fibers provides, within a relatively small volume, a large amount of surface area upon which the cells can grow. This large amount of surface area also facilitates localized distribution of nutrient media to the growing cells and ready collection of cell waste products. Shell-and-tube type bioreactors enable the growth of cells at much higher density rates than is possible with other cell culture devices. They can support cell densities greater than $10^8$ cells per milliliter, whereas other cell culture devices are typically limited to densities around $10^6$ cells per milliliter.

A further aspect of the invention provides a device for the extracorporeal treatment of body fluids, comprising cells and a membrane of the invention. In one embodiment, the cells are adherent cells which form a confluent layer on a surface of the membrane, for instance the surface of the lumen of a hollow fiber membrane of the invention, or the outer surface of a hollow fiber membrane of the invention. For the rest, the design of the device can be similar to the design described above for the cell culturing device. The body fluid to be treated is conducted through a fluid space of the device where it passes over the cell layer, allowing the cells to extract components from the body fluid, to metabolize components of the body fluid, or to segregate components into the body fluid.

EXAMPLES

The assessment of the suitability and efficiency of the membranes of the invention was based, in general, on the following principal characteristics: cell expansion rate, re-attachment efficiency of cells onto membranes, and characteristics of the cells' post expansion including morphology control. Tests were performed with mesenchymal stem cells (MSC), fibroblasts, epithelial cells and hepatocytes in order to prove that the membranes according to the present invention are suitable for the culturing of various adhesive cell types. MSC were chosen for the in depth analysis of the performance of membranes of the invention for cell culture.

Methods

Preparation of Hand Bundles, Mini-Modules, Filters and Flat Sheet Inserts (A) Hand Bundles The preparation of the membrane bundle after the spinning process is necessary to prepare the fiber bundle in an adequate way for succeeding performance tests. The first process step is to cut the fiber bundles to a defined length of 23 cm. The next process step consists of melting the ends of the fibers. An optical control ensures that all fibers are well melted. Then, the ends of the fiber bundle are transferred into a potting cap. The potting cap is fixed mechanically and a potting tube is put over the potting caps. Afterwards, the potting is done with polyurethane. After the potting is has to be ensured that the polyurethane can harden for at least one day. In the next process step, the potted membrane bundle is cut to a defined length and to open the ends of the fibers. The last process step consists of an optic control of the fiber bundle. During this process step, the following points are controlled: (i) quality of the cut (is the cut smooth or are there any damages of the knife), (ii) quality of the potting (is the number of open fibers of the spinning process reduced by fibers that are potted or are there any visible voids where the there is no polyurethane). After the optical control, the membrane bundles are stored dry before they are used for the different performance tests.

(B) Preparation of Mini-Modules

Mini-modules [=fiber bundles in a housing] are prepared with related process steps. The mini-modules are needed to ensure a protection of the fibers and a very clean manufacturing. The manufacturing of the mini-modules differs in the following points: (i) the fiber bundle is cut to a defined length of 20 cm; (ii) the fiber bundle is transferred into the housing before the melting process; (iii) the mini-module is put into a vacuum drying oven over night before the potting process.

(C) Preparation of Filters

The filter comprises about 8.000 to 15.000 fibers with an effective surface area of 0.9 to 1.7 m². A filter is characterized by a cylindrical housing with two connectors for the supplying culture medium fluid and applied caps on both sides, each with one centered connector. The manufacturing process (after winding) can be split up into the following main steps: (i) the cut (length of approx. 30 cm) bundles are transferred into the housing with a special bundle claw; (ii) both ends of the bundles are closed by a closing process; (iii) the fibers are potted into the housing with Polyurethane (PUR); (iv) the ends are cut to open the fibers, wherein a smooth surface is required; (v) the ends are inspected visually for closed fibers or imperfections in the PUR block; (vi) the caps are glued to the connectors; (vii) final treatment: rinsing, integrity testing, final drying; (viii) packaging in special bags for further steps (e.g. irradiation)

(D) Preparation of Flat Sheet Inserts

Flat membranes are immobilized on glass plates. Polyurethane functioning as glue for inserts is evenly distributed on a plate. The inserts are gently immersed in polyurethane and immediately glued onto the respective membrane. Inserts are weighed down with a glass and iron plate and dried for 16 to 18 hours. Flat membrane inserts are cut out and welded into sterilization bags. Finally, inserts may be sterilized in an autoclave at 121° C.

Hydraulic Permeability (Lp) of Hand Bundles and Mini-Modules

The hydraulic permeability of a membrane bundle is determined by pressing an exact defined volume of water under pressure through the membrane bundle, which has been sealed on one side, and measuring the required time. The hydraulic permeability can be calculated from the determined time, the effective membrane surface area, the applied pressure and the volume of water pressed through the membrane. From the number of fibers, the fiber length as well as the inner diameter of the fiber, the effective membrane surface area is calculated. The membrane bundle has to be wetted thirty minutes before the Lp-test is performed. For this purpose, the membrane bundle is put in a box containing 500 ml of ultapure water. After 30 minutes, the membrane bundle is transferred into the testing system. The testing system consists of a water bath that is tempered at 37° C. and a device where the membrane bundle can be implemented mechanically. The filling height of the water bath has to ensure that the membrane bundle is located underneath the water surface in the designated device. To avoid that a leakage of the membrane leads to a wrong test result, an integrity test of the membrane bundle and the test system has to be carried out in advance. The integrity test is performed by pressing air through the membrane bundle that is closed on one side of the bundle. Air bubbles indicate a leakage of the membrane bundle or the test device. It has to be checked if the leakage can be associated with the wrong implementation of the membrane bundle in the test device or if a real membrane leakage is present. The membrane bundle has to be discarded if a leakage of the membrane is detected. The applied pressure of the integrity test has to be at least the same value as the applied pressure during the determination of the hydraulic permeability in order to ensure, that no leakage can occur during the measurement of the hydraulic permeability because of a too high-applied pressure.

Diffusive Permeability of Hand Bundles

Diffusion experiments with isotonic chloride solution as well as phosphate diluted in dialysis fluid (100 mg/l) are carried out to determine the diffusion properties of a membrane. A hand bundle is put in a measuring cell. The measuring cell allows passing the particular solution at the inside of the hollow fiber. Additionally, the measuring cell is filled completely with water and a high cross flow of distilled water is set to carry away the particular ions that pass the membrane cross section from the inside of the hollow fiber to the outside. By adjusting the pressure ratios correctly, a zero filtration is aimed for, so that only the diffusion properties of the membrane are determined (by achieving the maximum concentration gradient of the particular ion between the inside of the hollow fiber and the surrounding of the hollow fiber) and not a combination of diffusive and convective properties. A sample from the pool is taken at the beginning and a sample of the retentate is taken after 10 and 20 minutes. The chloride samples are then titrated with silver nitrate solution to determine the chloride concentration. The phosphate samples are analyzed photometrically. From the concentrations determined, the effective membrane surface area A and the flow conditions, the permeability P, of chloride or phosphate, respectively, can be calculated according to the following equation (2):

$$P_x[10^{-4} \text{ cm/s}] = [Q_B/60/A]*\ln[(c_A-c_D)/c_R]*10^4 \qquad (2)$$

with

P=diffusive permeability [cm/s]
c=concentration [mmol]
A=effective membrane surface [cm²]

indices:
    x=substance (here: chloride or phosphate, respectively)
    A=starting concentration (feed)
    D=dialysate
    R=retentate
$Q_B$=blood flow [ml/min]

Sieving Coefficient for Myoglobin in Aqueous Solution (Hand Bundle)

The Sieving Coefficient experiments in aqueous solution of myoglobin and albumin are performed using two different experimental set-ups with separate solutions. As a first test the sieving coefficient of myoglobin is determined.

The concentration of myoglobin dissolved in PBS buffer is 100 mg/L. The expiry date of the aqueous solution is between 4 and 8 weeks. The solution has to be stored in the refrigerator. Prior to the Sieving Coefficient experiment, Lp-test is done using the method described earlier. The myoglobin sieving coefficient experiment is run in single pass whereas testing conditions are defined as follows: The intrinsic flow rate ($J_v$ in cm/s) and wall shear rate ($\gamma$ in s$^{-1}$) are fix whereas the blood flow ($Q_B$) and filtration rate (UF) is calculated (see equation (4)+(5)):

$$Q_B \text{ [ml/min]} = \gamma * n * \pi * d_i^3 * 60/32 \quad (4)$$

$$UF \text{ [ml/min]} = J_v * A * 60 \quad (5)$$

with
    n=amount of fibers
    $d_i$=inner diameter of fiber [cm]
    $\gamma$=shear rate [s$^{-1}$]
    A=effective membrane surface [cm$^2$]
whereas A is calculated according to equation (1):

Testing a hand bundle or a mini-module the shear rate is set to 500 s$^{-1}$ and the intrinsic flow rate is defined to be $0.38 \cdot 10^{-04}$ cm/s.

The first samples are taken after 15 minutes (pool, retentate, and filtrate) and a second time after 60 min. At the end, the test-bundle is rinsed for some minutes with PBS-buffer then the test is stopped.

Example 1

Preparation of a Flat Sheet Membrane

A polymer solution was prepared by dissolving polyethersulfone (Ultrason® 6020, BASF), polyvinylpyrrolidone (K30 and K85, BASF), polyurethane (Desmopan® 9665 DU, Bayer MaterialScience AG) as well as distilled water in N-methylpyrrolidone (NMP) at 60° C. until a clear, highly viscous solution was obtained.

The weight fraction of the different components in the polymer spinning solution, PES/PVP(K85)/PVP(K30)/9665DU/H$_2$O/NMP was 14/3/5/2/3/73. The viscosity of the resulting polymer solution was 21,000 mPa·s.

The solution was filtrated and degassed. Degassing of the polymer solution was performed in a drying oven at increased temperature (<100° C.) and reduced pressure (approximately 100 mbar). The final polymer solution was then cast (automatically) as an uniform film onto a smooth surface (glass slide) which acted as supporting area by utilizing a special coating knife. First, the polymer solution was heated to 60° C. in an oven and then directly applied steady-going onto the glass slide using a syringe. The coating knife with a defined height of gap (100 μm) was driven with a constant velocity of 12.5 mm/s, thus creating a uniform polymer film. This glass slide with the thin polymer film was quickly dipped into the coagulation bath.

As coagulation bath, a water/NMP mixture containing 56 wt.-% water and 44 wt.-% NMP was used at 50° C. The precipitation of the membrane took about 5 minutes. Subsequently, the precipitated membrane was taken out, stored in non-solvent until all membranes of a series were prepared and then cut to a defined size. After cutting, the membranes were washed with distilled water for 30 minutes at 70° C. The following steps were drying in an oven at 60° C. over night and finally packaging the membranes in special bags used for sterilization. The membrane thickness was 35 μm.

Example 2

Preparation of a Flat Sheet Membrane

A polymer solution was prepared by dissolving polyethersulfone (Ultrason® 6020, BASF), polyvinylpyrrolidone (K30 and K90, BASF), as well as distilled water in N-methylpyrrolidone (NMP) at 60° C. until a clear, highly viscous solution was obtained.

The weight fraction of the different components in the polymer spinning solution, PES/PVP(K90)/PVP(K30)/H$_2$O/NMP was 13.6/2/5/3/76.4. The viscosity of the resulting polymer solution was 5,900 mPa·s.

A membrane was prepared as described in Example 1. The membrane thickness was 50 μm.

Example 3

Preparation of a Hollow Fiber Membrane

A polymer solution was prepared by mixing 13.5% of polyethersulfone, 0.5% of polyamide, 7.5% of PVP K30 and 78.5% of NMP. A mixture of 59 wt.-% water and 41 wt.-% NMP served as center fluid. The viscosity of the polymer solution, measured at a temperature of 22° C. was 4,230 mPa·s.

The center fluid was heated to 55° C. and pumped through a two-component hollow fiber spinneret. The polymer solution was leaving the spinneret through an annular slit with an outer diameter of 0.5 mm and an inner diameter of 0.35 mm. The center fluid was leaving the spinneret in the center of the annular polymer solution tube in order to start the precipitation of the polymer solution from the inside and to determine the inner diameter of the hollow fiber.

At the same time the two components (polymer solution and center fluid) were entering a space separated from the room atmosphere. The space is called spinning shaft. A mixture of steam (100° C.) and air (22° C.) was injected into the spinning shaft. The temperature in the spinning shaft was adjusted to 49° C. and a relative humidity of 99.5% by the ratio of steam and air and the solvent content therein was adjusted to 3.9 wt.-%, related to the water content. The solvent was NMP. The length of the spinning shaft was 890 mm. By the aid of gravity and a motor-driven roller, the hollow fiber was drawn from top to bottom, from spinneret through the spinning shaft into a water bath in vertical direction. The spinning velocity was 50 m/min. The hollow fiber was subsequently led through a cascade of water baths and temperatures increasing from 20 to 90° C. The wet hollow fiber membrane leaving the water-rinsing bath is dried in a consecutive online drying step. After an optional texturizing step, the hollow fiber was collected on a spinning wheel in the shape of a bundle. The outer surface of the hollow fiber according to this example had 62,500 pores per mm$^2$ having a pore diameter in the range of 0.5 to 3 μm.

Example 4

Preparation of a Hollow Fiber Membrane

A polymer solution was prepared by mixing 14.0 wt.-% of polyethersulfone, 5.0 wt.-% of PVP K30, 2.0 wt.-% of PVP K85/K90, 3 wt.-% of water and 76.0% of NMP. A mixture of 55 wt.-% water and 45 wt.-% NMP served as center fluid. The viscosity of the polymer solution, measured at a temperature of 22° C., was 5,400 mPa·s.

The center fluid was heated to 55° C. and pumped through a two-component hollow fiber spinneret. The polymer solution was leaving the spinneret through an annular slit with an outer diameter of 0.5 mm and an inner diameter of 0.35 mm. The center fluid was leaving the spinneret in the center of the annular polymer solution tube in order to start the precipitation of the polymer solution from the inside and to determine the inner diameter of the hollow fiber. At the same time the two components (polymer solution and center fluid) were entering a space separated from the room atmosphere. The space is called spinning shaft. A mixture of steam (100° C.) and air (22° C.) was injected into the spinning shaft. The temperature in the spinning shaft was adjusted to about 45° C. and a relative humidity of 99.5% by the ratio of steam and air. The length of the spinning shaft was 890 mm. By the aid of gravity and a motor-driven roller, the hollow fiber was drawn from top to bottom, from spinneret through the spinning shaft into a water bath in vertical direction. The spinning velocity was 50 m/min. The hollow fiber was subsequently led through a cascade of water baths and temperatures increasing from 15 to 40° C. The wet hollow fiber membrane leaving the water-rinsing bath was dried in a consecutive online drying step. After a texturizing step, the hollow fiber was collected on a spinning wheel in the shape of a bundle. Alternatively, hand bundles can be formed.

Example 5

Preparation of a Hollow Fiber Membrane

A polymer solution was prepared by dissolving polyethersulfone (Ultrason® 6020, BASF), polyvinylpyrrolidone (K30 and K85, BASF), polyurethane (Desmopan® PU 9665 DU, Bayer MaterialScience AG) as well as distilled water in N-methylpyrrolidone (NMP) at 50° C. until a clear, highly viscous solution was obtained.

The weight fraction of the different components in the polymer spinning solution, PES/PVP(K85)/PVP(K30)/9665 DU/$H_2$O/NMP was 14/3/5/2/3/73. The viscosity of the polymer solution was 22,900 mPa·s.

The warm solution was cooled to 20° C. and degassed. A membrane was formed by heating the polymer solution to 50° C. and passing the solution through a spinning die. As bore liquid, a water/NMP mixture containing 56 wt.-% water and 44 wt.-% NMP was used. The temperature of the die was 50° C. The hollow fiber membrane was formed at a spinning speed of 40 m/min. The liquid capillary leaving the die was passed into a water bath having ambient temperature. The length of the distance between the die and the precipitation bath was 100 cm. The formed hollow fiber membrane was guided through a series of water baths. The wet hollow fiber membrane was then dried and had an inner diameter of 216 µm and an outer diameter of 318 µm. The membrane had a fully asymmetric membrane structure. The active separation layer of the membrane was at the inner side. The active separation layer was defined as the layer with the smallest pores. The structure shows an overall sponge like structure. The inner surface shows very smooth pores. The membranes were wound on a winding wheel and hand bundles with 200 fibers were prepared according to the method described below. The hydraulic permeability (Lp value) of the membrane was measured on hand. The membrane showed a hydraulic permeability of $3.7 \times 10^{-4}$ cm$^3$/(cm$^2$ bar sec). Additionally, the sieving coefficient of myoglobin (in aqueous solution) was measured. A sieving coefficient of 1.5% was obtained after 15 minutes and a sieving coefficient of 1.1% was obtained after 60 minutes. Subsequently, the hydraulic permeability (Lp value) of the membrane was measured again and was $2.7 \times 10^{-4}$ cm$^2$/(cm$^2$ bar sec) at 37° C. Furthermore, experiments regarding the diffusive permeability of the membrane were performed with chloride, inulin and vitamin $B_{12}$. The permeability for chloride, inulin and vitamin $B_{12}$ was $10.5 \times 10^{-4}$ cm/sec, $3.7 \times 10^{-4}$ cm/sec and $4.0 \times 10-4$ cm/sec, respectively, at 37° C.

Example 6

Irradiation of Inserts and Preparation for Cell Culture

Air-covered membranes (oxygen concentration was not increased or lowered) were subjected to gamma irradiation (25 and 75 kGy, respectively) in conventional sterilization bags for 6.3 and 18.9 h, respectively, at room temperature.

Water- or acrylic acid solution-covered membrane inserts were subjected to gamma irradiation in plastic containers containing approximately 70 ml solution. For washing of fluid-covered membrane inserts, dishes for each membrane type containing approximately 300 ml conventional PBS medium (8 g NaCl, 0.2 g KCl, 1.44 g Na$_2$HPO$_4$, 0.24 g KH$_2$PO$_4$ in 800 ml of distilled H$_2$O, adjusted to a pH of 7.4 with HCl, H$_2$O added to 1 liter and sterilized by autoclave) were prepared. Inserts were sterilely removed from the container, washed in the PBS dish, and transferred to 6-well plates for further rinsing. All insert types were transferred to 6-well plates and were rinsed five times on the top and bottom side with 3 ml and 5 ml PBS, respectively. For each rinsing step, inserts were incubated at least 10 min in order to remove residual reagents and side products generated during gamma irradiation. After having finished the rinsing procedure, inserts were transferred to new well plates for cell culture. 3 ml MSC medium were added to the top side and 5 ml to the bottom side of the insert in the well, respectively. Inserts were incubated in MSC medium in an incubator overnight.

Fibronectin-coated membranes (based on membranes according to Example 2), to be used for comparison, represented an exception. Washing and rinsing of the inserts was performed as described above. 1 ml PBS buffer containing 21 µg fibronectin was added to the top of the insert and incubated in an incubator overnight. The next day, the fibronectin solution was removed and inserts were washed once with PBS, and incubated with cell medium overnight prior to cell seeding. Untreated membrane inserts (Example 2) and TCPS culture plates were used as negative and positive control, respectively.

Example 7

Irradiation of Hollow Fiber Membranes

Bioreactors (hollow fibers in a housing) which were subjected to gamma-ray irradiation consisted of membranes of the invention in hollow fiber geometry (see Examples 4 to 6). The materials for housing, headers, and potting were gamma-stable and consisted of Makrolon® DP1-1262 (Bayer MaterialScience AG) with Fibasol blue (housing/headers) and gamma-stable polyurethane (potting). Bioreactors containing PES/PVP/PA-based membranes (see Example 4) were filled with ambient air, water (RO-water), an aqueous solution of 0.001% acrylic acid (0.01 g AA in 1 l RO-water) or an aqueous solution of 0.01% acrylic acid (0.1 g AA in 1 l RO-water), and subjected to gamma irradiation applying 25 or 75 kGy. The filling of the reactors with aqueous solutions and water was performed by flushing from the intracapillary (IC) side with 100 ml/min, and air was removed. The IC-out-line was clamped and the extracapillary (EC) side was filled by ultrafiltration. The steps were repeated until no residual air remained in the bioreactor. Gamma irradiation was done with a Co-60 source applying 25 or 75 kGy for 6.3 and 18.9 hours at room temperature.

Example 8

Culturing of Unprocessed Bone Marrow on Flat Sheet Membranes

MSC medium (900 ml alpha-MEM medium (Lonza, Cat.-No. BE12-169F), 100 ml FBS, 10 ml penicillin/streptomycin, and 10 ml ultraglutamine I; prior to cell culture use, the MSC medium was warmed up to 37° C.) was replaced after overnight incubation on insert membranes by fresh MSC medium in top (2 ml) and bottom side (4 ml) of insert. Those medium volumes were applied in all further steps. Respective volumes of unprocessed bone marrow were added to each insert as indicated in Table I. Bone marrow was homogenously distributed on membrane by shaking the dish. Inserts were placed into incubator for 3 days to allow for MSC adhesion. On day 3, the medium was removed from top and bottom side of insert culture. Membranes were rinsed twice with 2 ml PBS for each rinsing step on top side. Fresh MSC medium was added to top and bottom side. In a first growth phase (i.e. culture phase from bone marrow seeding to first MSC detachment), the medium was exchanged in top and bottom side of inserts every 2 to 3 days until day 12 or 14. On day 12 or 14, the MSCs were detached using 500 µl trypsin (10 min, 37° C.) per insert from 3 of the 4 inserts. Trypsin was inactivated using 1.5 ml MSC medium per insert, the MSC suspension was collected in sterile tube and samples were taken for MSC counting using a CASY counter. One of the 4 inserts was fixed and prepared for SEM. Therefore, the insert was washed on the top side once with PBS, 1 ml of a 2% glutaraldehyde solution was added and stored overnight at 4° C. Subsequently, the inserts were washed three times with distilled water, air-dried and subjected to SEM. In the second experiments, a SEM was not performed. Fresh medium was added to top and bottom side of same inserts after pre-warming and conditioning of the MSC medium with gas in incubator until re-seeding of MSCs. 10,500 MSCs/cm² were allowed to re-attach overnight onto the same inserts. In the second growth phase, re-attached MSCs were expanded on membranes for additional 7 days. MSC medium was exchanged every 2 to 3 days. MSCs were harvested from 3 inserts of 4 inserts on day 19 or 21 using trypsin for 10 min at 37° C. MSCs were re-plated on TCPS for control of MSC morphology and proliferation potential. Therefore, harvested MSCs were reseeded on TCPS at 5,000 MSCs/cm² for control of morphology and at 500 MSCs/cm² for control of proliferation control for 4 or 5 days. Morphology and proliferation potential were recorded by taking microscopic pictures on day 1 or 2 for morphology assessment and on day 4 or 5 for assessment of proliferation potential.

Figure 2:
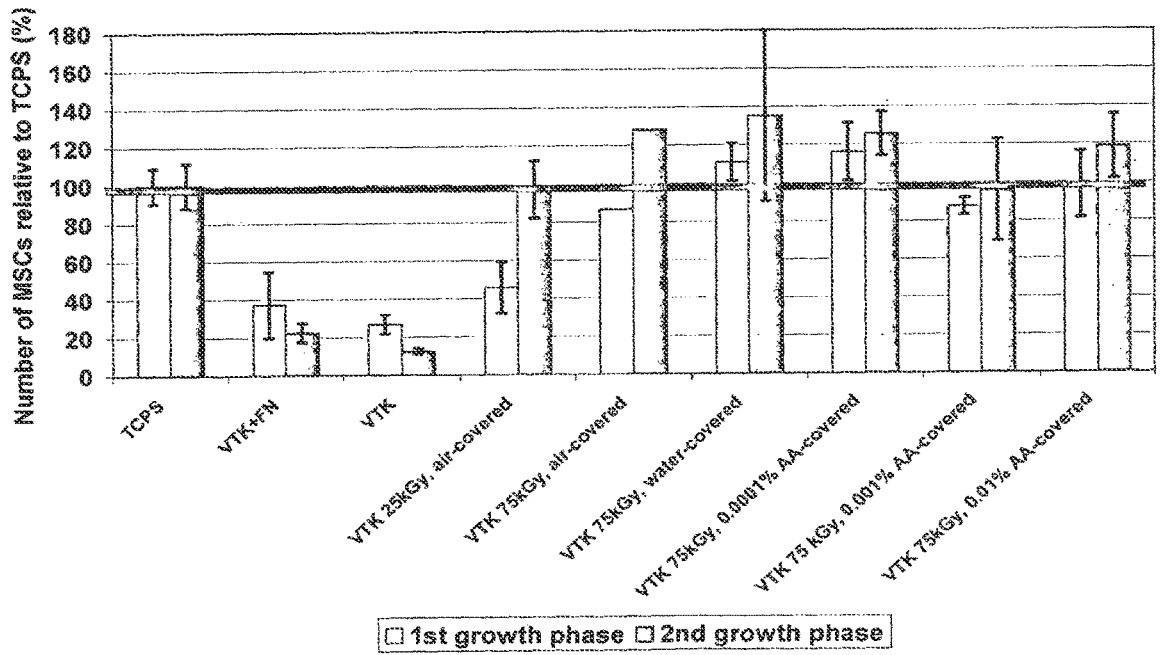
FIG. 2 shows the number of MSC grown from unprocessed bone marrow on various membrane types relative to the number of MSC grown on standard TCPS after the first (14 days) and second (7 days) growth phase in [%] (Experiment 2). The horizontal line indicates TCPS level. For the abbreviations used see Table I.

Unprocessed bone marrow was plated onto various substrates (Table I). TCPS or VTK-FN (fibronectin-coated) and VTK (steam sterile, uncoated) were used as positive and negative controls, respectively. After the first growth phase of 12-14 days, cells were trypsinized and counted. Respective MSC numbers relative to TCPS are represented by light-colored bars in FIGS. 1 and 2. For the second growth phase, MSC were re-plated at a density of 500 MSC/cm² onto same inserts and expanded in a second growth phase for additional 10 days. After the second growth phase of 7 days, determination of MSC numbers (represented by black bars in FIGS. 1 and 2), re-plating for morphology (FIG. 3) and fixation for SEM were performed. The number of MSC (n=3) relative to TCPS as standard is shown in FIGS. 1 and 2, the line indicates standard TCPS level. Experiments with unprocessed bone marrow were performed twice.

TABLE I

Overview of membrane types and irradiation conditions used for the cultivation of MSC from unprocessed bone marrow.

| Membrane | Bone marrow volume (µl) | n | Total bone marrow volume (µl) |
|---|---|---|---|
| TCPS | 300 | 3 | 900 |
| VTK (untreated) | 150 | 4 | 600 |
| VTK + FN coating | 150 | 4 | 600 |
| VTK 25 kGy, air-covered | 150 | 4 | 600 |
| VTK 75 kGy, air-covered | 150 | 4 | 600 |
| AN96ST (untreated) | 150 | 4 | 600 |
| VTK 75 kGy, water-covered | 150 | 4 | 600 |
| VTK 75 kGy, water-covered with 0.0001% AA | 150 | 4 | 600 |
| VTK 75 kGy, water-covered with 0.001% AA | 150 | 4 | 600 |
| VTK 75 kGy, water-covered with 0.01% AA | 150 | 4 | 600 |

"n" indicates the number of tests performed for each set-up.
"AA" represents "acrylic acid".
The expression "VTK" represents a membrane based on the polymer solution used in Example 2.
"FN" represents "fibronectin".
The membrane AN69ST ™ is a commercial membrane based on polyacrylonitrile.

Figure 3:
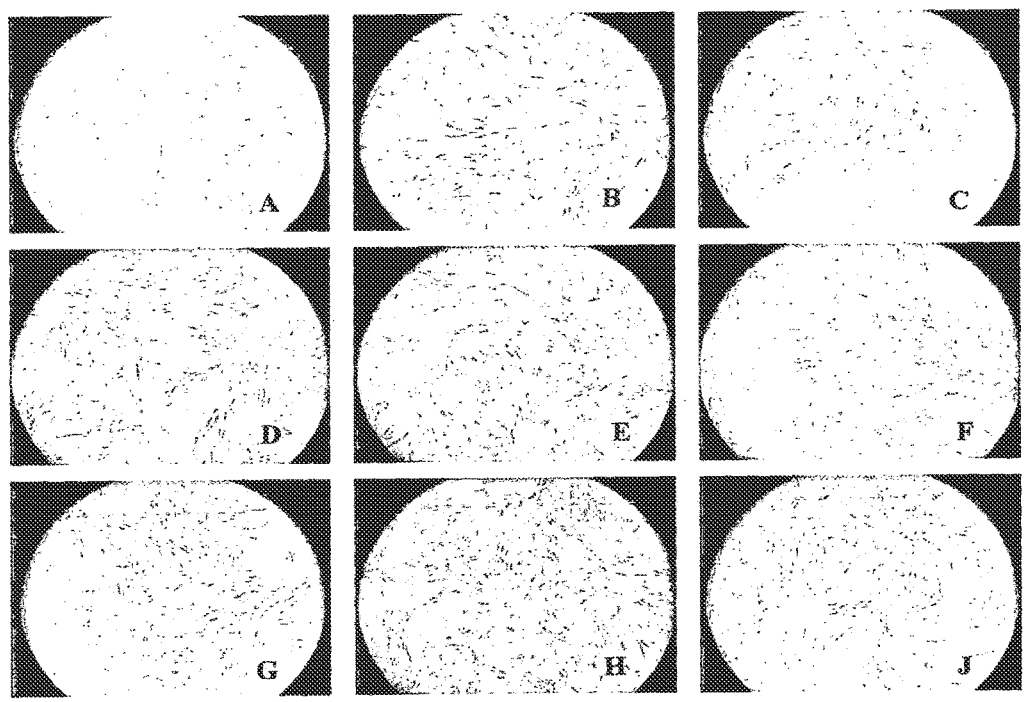
FIG. 3 shows the morphology of re-plated MSC on conventional TCPS dishes on day 5 of the second growth phase. The MSC are derived from Experiment 2 as described in Example 10. Abbreviations are as described in Table I. (A) VTK membrane, water covered, 0% acrylic acid, 75 kGy. (B) VTK membrane, water covered, 0.0001% acrylic acid, 75 kGy. (C) VTK membrane, water covered, 0.001% acrylic acid, 75 kGy. (D) VTK membrane, water covered, 0.01% acrylic acid, 75 kGy. (E) TCPS. (F) VTK membrane, air-covered, 25 kGy. (G) VTK membrane, air-covered, 75 kGy. (H) VTK membrane, untreated. (J) VTK membrane+ FN coating.

As can be seen from FIGS. 1 through 3, MSC showed growth on fibronectin-coated VTK membranes in the first growth phase of comparable to, i.e. fibronectin-coated VTK membranes are not suitable for a re-seeding culture. The reason for the lack of performance of fibronectin-coated membranes after trypsinization is assumed to be degradation of fibronectin by trypsin. In Experiment 2 (FIG. 2), fibronectin-coated VTK membranes did work in neither the first nor the second growth. Uncoated VTK membranes showed very weak growth of MSC in both experiments. Air-covered VTK inserts irradiated with 25 kGy showed controversial results comparing Experiments 1 and 2; in FIG. 1, this membrane type performed comparable to TCPS in the first growth phase but showed a strong decrease of MSC in the second growth phase, whereas the membrane type behaved vice versa in Experiment 2. Air-covered VTK inserts irradiated with 75 kGy showed MSC growth in both growth phases comparable or better than TCPS. Coverage of VTK membranes with water or aqueous acrylic acid solution with different concentrations during the gamma irradiation procedure resulted in similar results as air-covered VTK inserts irradiated with 75 kGy. AN69ST inserts were included in experiment 1 and proved to be unsuitable for MSC culture.

Re-plated MSC after second growth phase showed mostly spindle-shaped morphology and normal proliferation (see FIG. 3).

Example 9

Culturing of Pre-Processed MSC on Flat Sheet Membranes

MSC medium was replaced from inserts after overnight incubation by fresh medium on top and bottom sides of inserts. MSC were trypsinized from the flasks applying standard flask conditions for MSC (0.25% trypsin, 5 min, and 37° C., knocking until all cells are detached and inactivation of trypsin by addition of medium). MSC were counted using a CASY counter. A MSC suspension was prepared which allowed seeding 500 MSC/cm$^2$ in TCPS-wells or inserts. Well-plates and inserts were placed into an incubator to allow for MSC adhesion. The MSC medium was exchanged on the top and bottom side every 2 to 3 days until day 7 or 9 (aiming at up to ~80% confluence in TCPS). On day 7 and/or 9, MSC were detached by using 500 µl trypsin (10 minutes, 37° C.). Trypsin was then inactivated by using 1.5 ml MSC medium and MSC were collected as cell suspension in a sterile tube. Samples were taken for cell counting using a CASY counter. One insert was fixed and prepared for SEM. Therefore, inserts were washed on top side once with PBS, then 1 ml of a 2% glutaraldehyde solution was added and everything was stored overnight at 4° C. Subsequently, inserts were washed with distilled water, air-dried and subjected to SEM. Fresh MSC medium was added to the top (2 ml) and bottom side (4 ml) of the inserts. The medium was pre-warmed and conditioned with gas in an incubator until cell re-seeding. 500 MSC/cm$^2$ were re-attached overnight in incubator onto same inserts. Re-attached MSC were expanded on membranes for an additional 10 or 11 days. MSC medium was exchanged every 2 to 3 days. MSC were harvested from three inserts on day 16 or 21. MSC were re-plated on TCPS for control of MSC morphology and proliferation potential. Therefore, harvested MSC were re-seeded on TCPS at 5,000 MSC/cm$^2$ for control of morphology and at 500 MSC/cm$^2$ for control of proliferation potential for 4 or 5 days. Morphology and proliferation potential were recorded by taking microscopic pictures on day 1 or 2 for morphology assessment and on day 4 or 5 for assessment of proliferation potential. Table II gives an overview over all membrane types and modifications as well s over irradiation conditions used in these experiments.

TABLE II

Overview of membrane types and irradiation conditions used for the cultivation of pre-selected MSG.

| Membrane | Cell number (500 cells/cm$^2$) | n | Total cell number |
|---|---|---|---|
| TCPS | 4,800 | 3 | 14,400 |
| VTK (untreated) | 2,250 | 4 | 9,000 |
| VTK + FN coating | 2,250 | 4 | 9,000 |
| VTK 25 kGy, air covered | 2,250 | 4 | 9,000 |
| VTK 75 kGy air-covered | 2,250 | 4 | 9,000 |
| VTK 75 kGy water-covered | 2,250 | 4 | 9,000 |
| VTK 75 kGy, water-covered with 0.0001% AA | 2,250 | 4 | 9,000 |
| VTK 75 kGy, water-covered with 0.001% AA | 2,250 | 4 | 9,000 |
| VTK 75 kGy, water-covered with 0.01% AA | | | |

"n" indicates the number of tests performed for each setup.
"AA" represents "acrylic acid".
The expression "VTK" represents a membrane based on the polymer solution used in Example 2.
"FN" represents "fibronectin".

Figure 4:
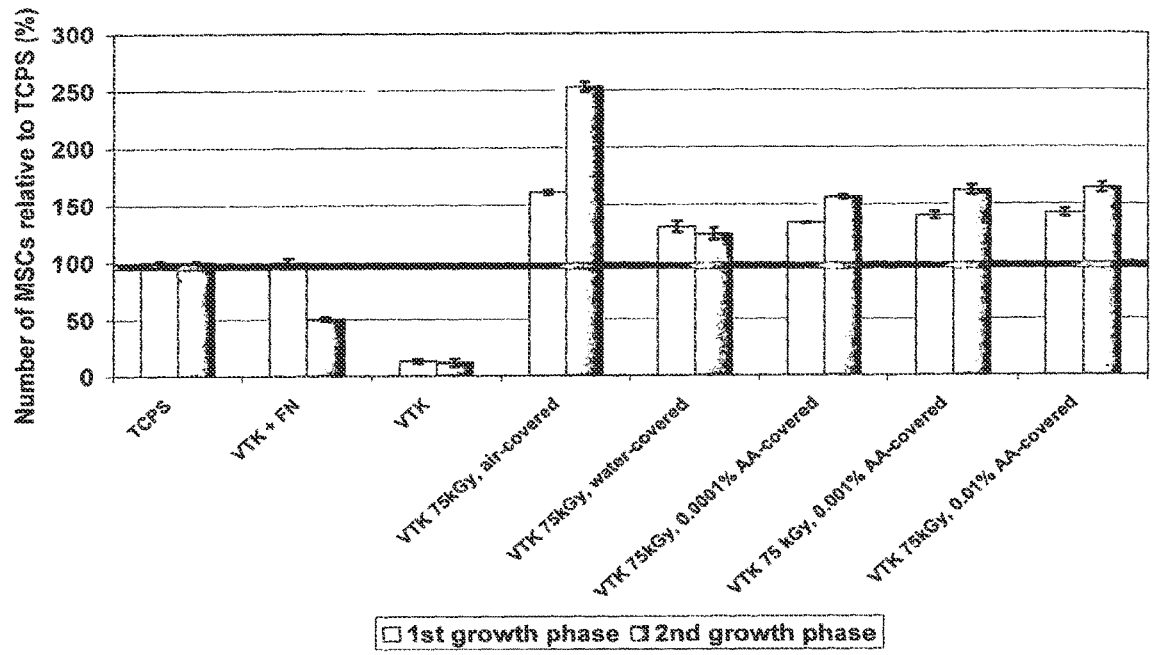
FIG. 4 shows the number of MSC grown from pre-selected MSC on various membrane types relative to the number of MSC grown on standard TCPS after the first (9 days) and second (7 days) growth phase in [%] (Experiment 1). The horizontal line indicates TCPS level. For the abbreviations used see Table II and Example 11.
Figure 5:
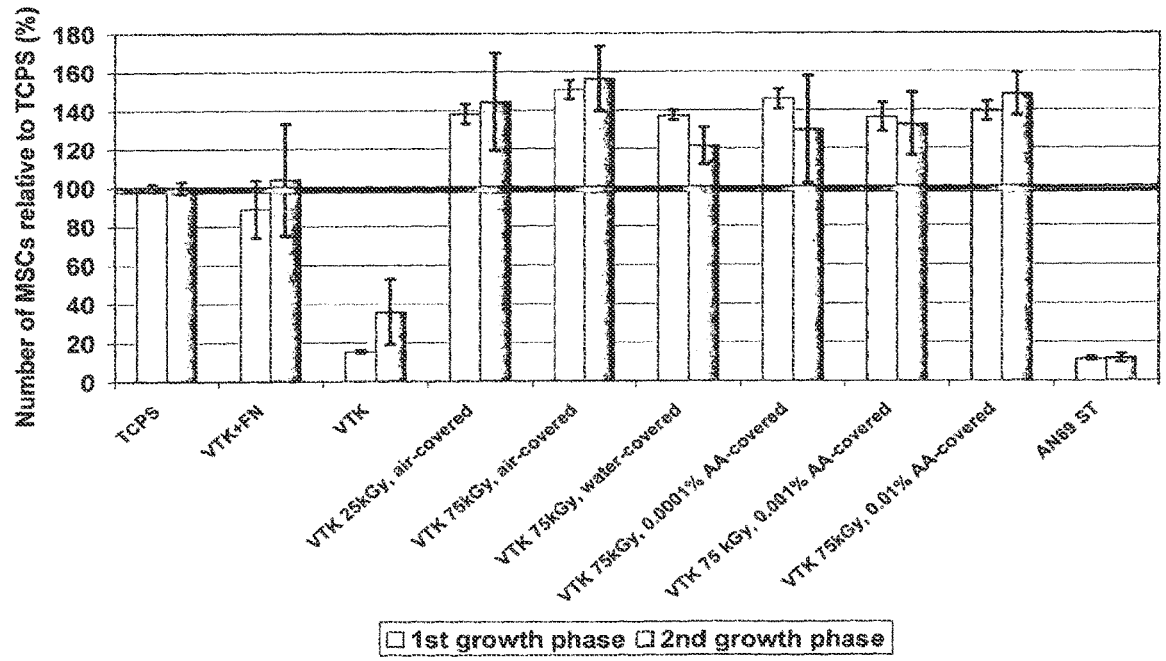
FIG. 5 shows the number of MSC grown from pre-selected MSC on various membrane types relative to the number of MSC grown on standard TCPS after the first (10 days) and second (11 days) growth phase in [%] (Experiment 2). The horizontal line indicates TCPS level. For the abbreviations used see Table II and Example 11.

Experiments using pre-selected MSC were done twice and results are shown in FIG. 4 (Experiment 1) and FIG. 5 (Experiment 2). MSC showed growth on fibronectin-coated VTK membranes in the first growth phase of Experiments 1 and 2 comparable to TCPS but showed strongly decreased growth in the second growth phase, i.e. fibronectin-coated membranes were not suitable for a re-seeding in Experiment 1. The reason for the lack of performance of fibronectin-coated membranes after trypsinization is assumed to be degradation of fibronectin by trypsin. Uncoated VTK membranes showed very weak growth of MSC in both experiments. Air-covered VTK inserts irradiated with 25 kGy were tested only in Experiment 2 and showed performance comparable to TCPS and comparable to all VTK membrane types after 75 kGy gamma irradiation. Air-covered VTK inserts irradiated with 75 kGy showed MSC growth in both growth phases comparable or in most cases better than TCPS. Coverage of VTK membranes with water or aqueous acrylic acid solution with different concentrations during the gamma irradiation procedure resulted in similar results as air-covered VTK inserts irradiated with 75 kGy. AN69ST inserts were included in Experiment 2 and proved to be unsuitable for MSC culture. Re-plated MSC on conventional TCPS dishes after second growth phase showed mostly spindle-shaped morphology and normal proliferation.

Example 11

Influence of Steam Sterilization Before Gamma Irradiation

Figure 6:
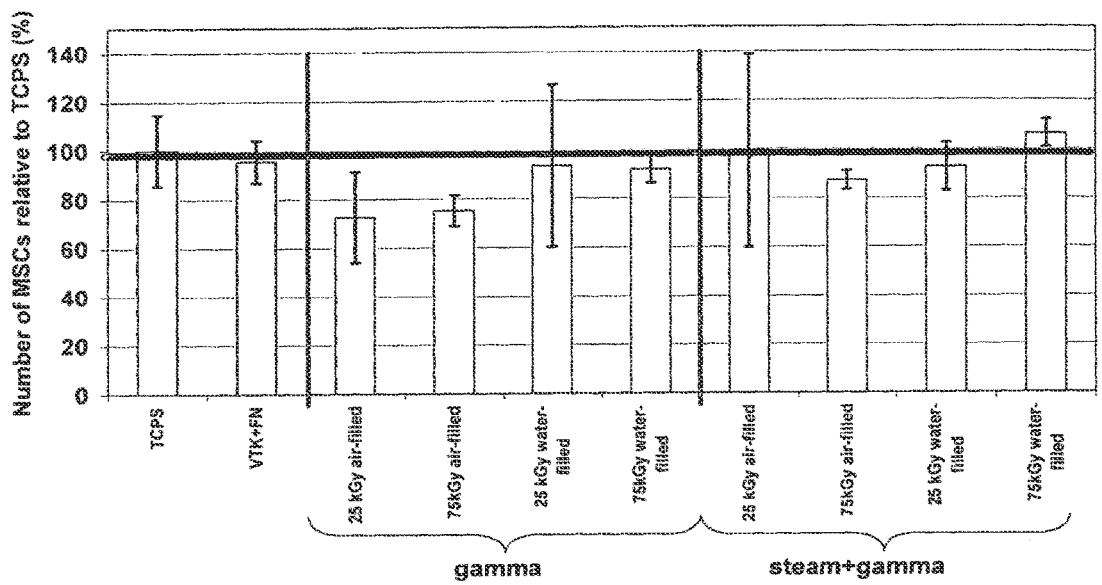
FIG. 6 shows a comparison of membranes which have been directly gamma-ray irradiated and membranes which were steam-sterilized before gamma-ray irradiation. The experiment as described in Example 12 is directed to the number of MSC which adhere to the surface of a given membrane relative to the number of MSC which adhere to a standard TCPS surface in [%]. The horizontal line depicts the TCPS level.

Experiments according to Example 10 were performed, wherein the number of MSC which adhered to the membrane surface relative to TCPS were determined in (%). Cell numbers were determined for TCPS and VTK membranes with fibronectin coating as well as for VTK membranes which had been irradiated with 25 or 75 kGy, either air-filled or water-covered. Three sets of experiments were performed. In a first setting, the membrane was directly gamma-ray irradiated after production. In a second setting, the membranes were steam-sterilized before they were subjected to the respective gamma-ray treatment. As can be seen from FIG. 6, membranes which had been steam-sterilized before gamma-ray irradiation performed better regarding the attachment of MSC compared to membranes without steam-sterilization.

Figure 7:
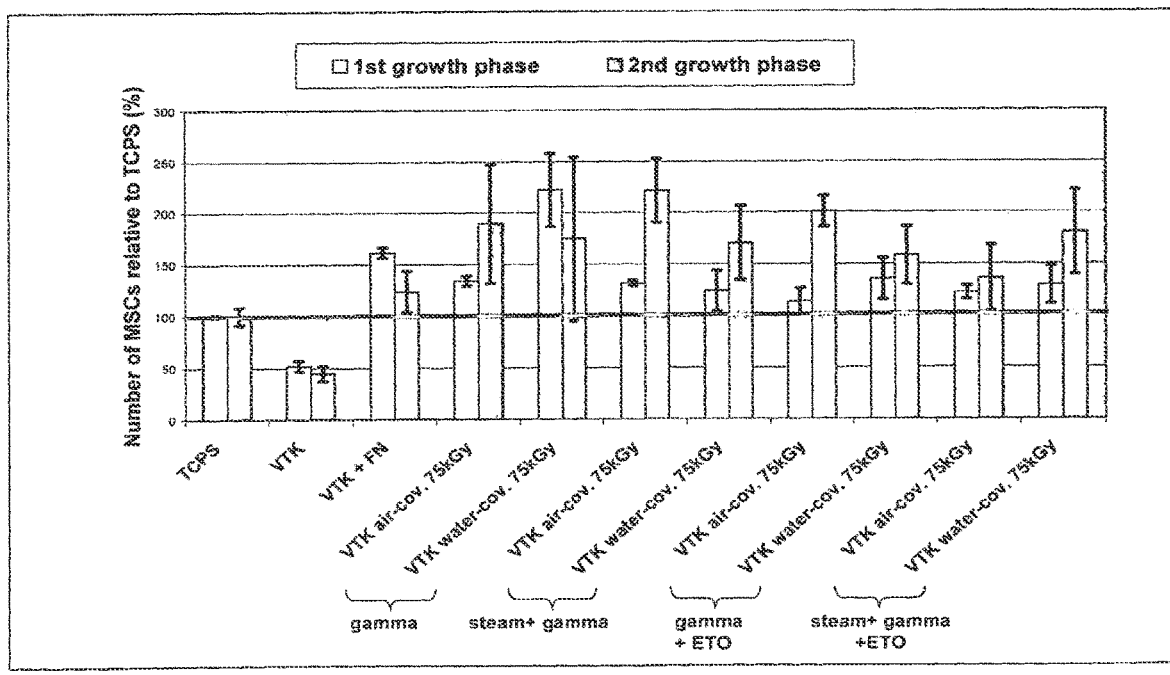
FIG. 7 shows the number of MSC grown from unprocessed bone marrow on membranes irradiated with 75 kGy with and w/o steam and ETO sterilization, relative to the number of MSC grown on standard TCPS after the first (11 days) and second (7 days) growth phase in [%]. The horizontal line indicates TCPS level.

In a third setting, the influence of an additional EtO sterilization step was investigated. The number of MSC grown from unprocessed bone marrow on membranes irradiated with 75 kGy with and w/o steam and ETO sterilization, relative to the number of MSC grown on standard TCPS after the first (11 days) and second (7 days) growth phase was determined. As can be seen from FIG. 7, EtO sterilization does not have a pronounced adverse effect on the performance of the membranes.

Example 12

Differentiation of Cells

In order to assess the differentiation ability of cells which have been cultivated on membranes according to the invention, adipogenesis and osteogenesis differentiation tests were performed to determine the ability of MSC to differentiate.

(A) Adipogenesis

Figure 8:
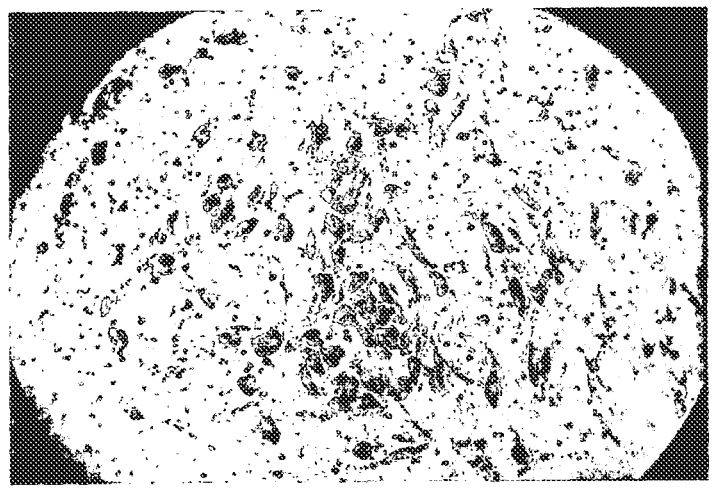
FIG. 8 shows the successful adipogenesis of MSC which were grown on membranes of the invention. (A) VTK membrane, water covered, 0.01% acrylic acid, 75 kGy. (B) VTK membrane, water covered, 0.01% allylamine, 75 kGy. (C) VTK membrane, water covered, 0.01% acrylic acid and 0.01% allylamine, 25 kGy.
Figure 8:
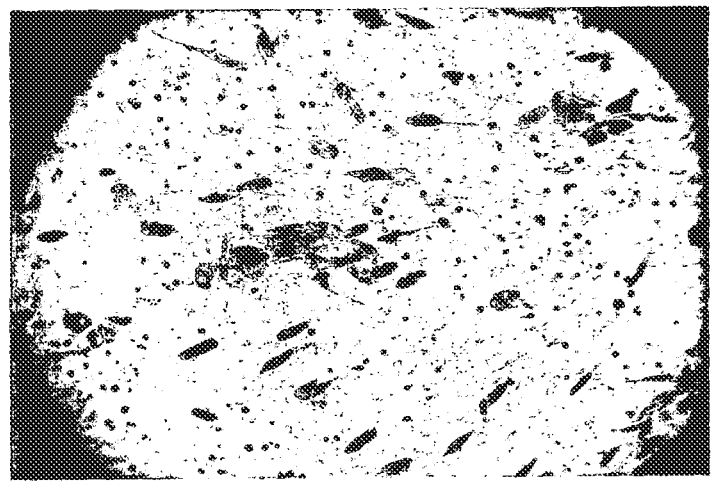
Figure 8:
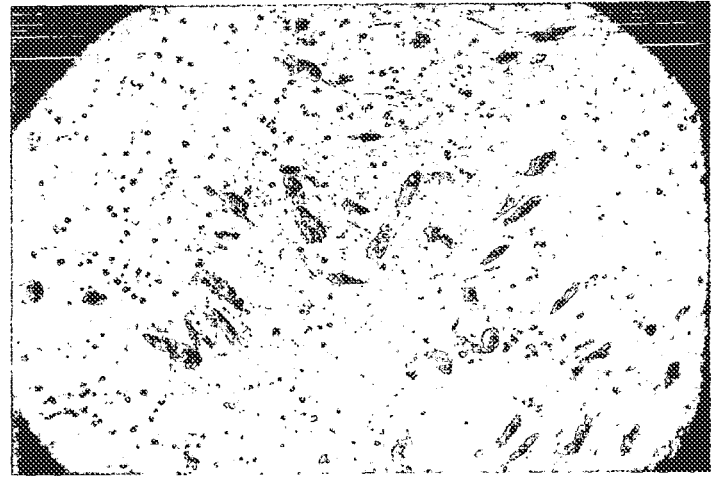

MSC were seeded into 24-well plates at a density of approx. 10,000 MSC/cm$^2$. Three wells used, one to differentiate MSC into adipocytes as described below, one to grow MSC in standard MSC expansion medium (without inducing adipogenesis) and another one as control for staining. MSC were grown to confluency or up to ten days over confluency using standard MSC expansion medium (900 ml alpha-MEM medium, 100 ml FBS, 10 ml penicillin/streptomycin, and 10 ml Ultraglutamine I; prior to cell culture use, MSC medium was warmed up to 37° C.). Adipogenesis was induced by using adipogenic induction medium (20 µl IBMX stock solution (55.55 mg IBMX dissolved in 10 ml distilled water, then 20 to 40 mg of sodium carbonate is added to the solution), 1 µl dexamethasone stock solution (19.62 mg dexamethasone in 50 ml pure ethanol), 1 µl insulin stock solution (10 mg/ml), and 2 µl indomethacine (178.9 indomethacine in 10 ml pure ethanol) in 1 ml standard MSC medium) for 11 days (day 0 to day 11). The medium was exchanged every 2-3 days. Adipogenic maintenance medium (1 µl insulin stock solution in 1 ml standard MSC medium) was used for 3 or 5 days (day 12-14 or day 12-16) and exchanged for every 2-3 days. Cells were rinsed with a standard PBS buffer. Cells were fixed by using a formaldehyde solution (~10%) for at least 4 hours at room temperature. Then, about 0.5 ml Oil Red O solution (freshly sterile-filtered) were added to each well, followed by incubation for 30 min to 2 hours at room temperature, rinsing the cells with PBS twice, followed by rinsing with 50% ethanol. The cells were counterstained with Mayer's hematoxylin solution for 5 min at room temperature, rinsed for 1 min with tap water, three times, and fixed with formaldehyde solution. FIG. 8 depicts the successful adipogenesis of MSC on cells which had been cultivated on gamma-ray irradiated (75 or 25 kGy, in the presence of acrylic acid or allylamine) VTK membranes.

(B) Osteogenesis

Figure 9:
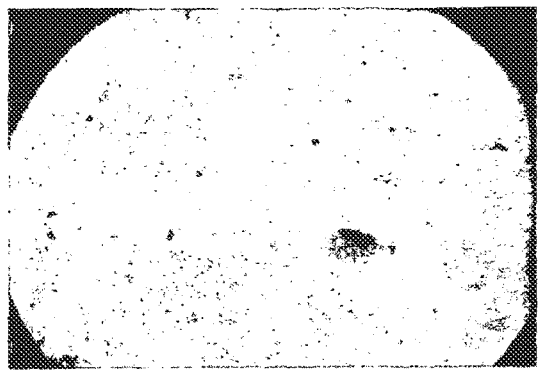
FIG. 9 shows the successful osteogenesis of MSC which were grown on membranes of the invention. (A) TCPS membrane (comparison). (B) VTK membrane, water covered, 0.01% acrylic acid, 75 kGy. (C) VTK membrane, water covered, 0.01% allylamine, 75 kGy. (D) VTK membrane, water covered, 0.01% acrylic acid+0.01% allylamine, 75 kGy. (E) VTK membrane, water covered, 0.01% acrylic acid, 25 kGy. (F) VTK membrane, water-covered, 0.5% acrylic acid, 25 kGy.
Figure 9:
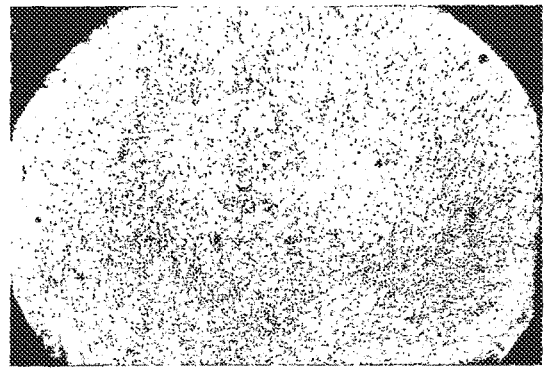
Figure 9:
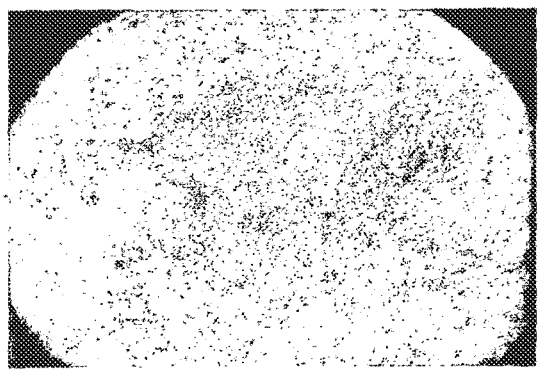
Figure 9:
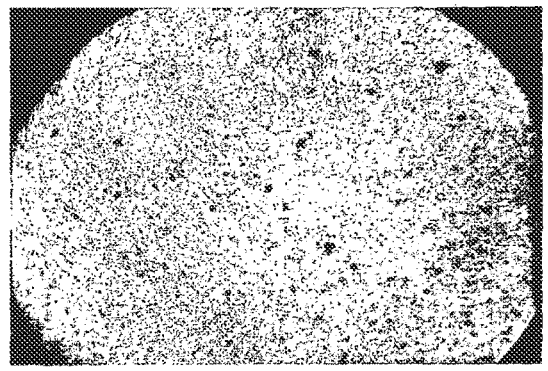
Figure 9:
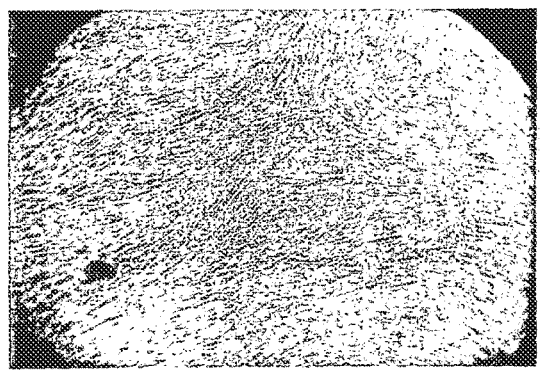
Figure 9:
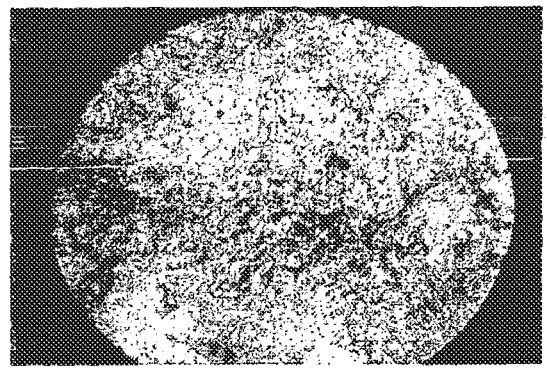
Figure 10:
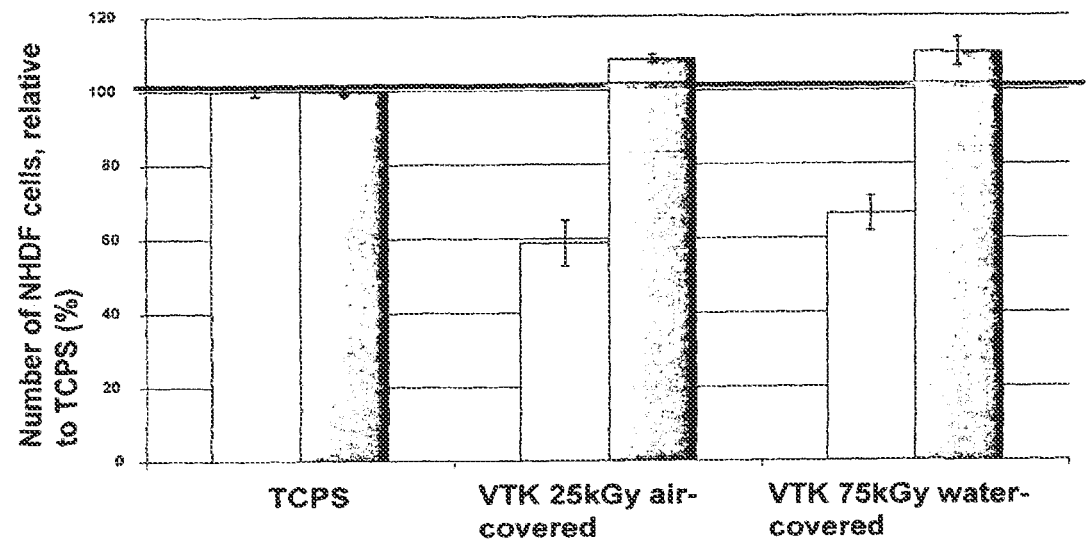
FIG. 10 shows the results of a short-term cell culture of human dermal fibroblasts (NHDF) on VTK membranes irradiated with 25 kGy (air-covered) or 75 kGy (water-covered) in comparison with TCPS. Left columns show the number of NHDF cells after 1 day relative to the number of cells on TCPS, i.e. they depict the efficiency of cell adhesion. Right columns show the number of NHDF cells after 5 days relative to the number of cells on TCPS, i.e. they depict the efficiency of cell proliferation.
Figure 11:
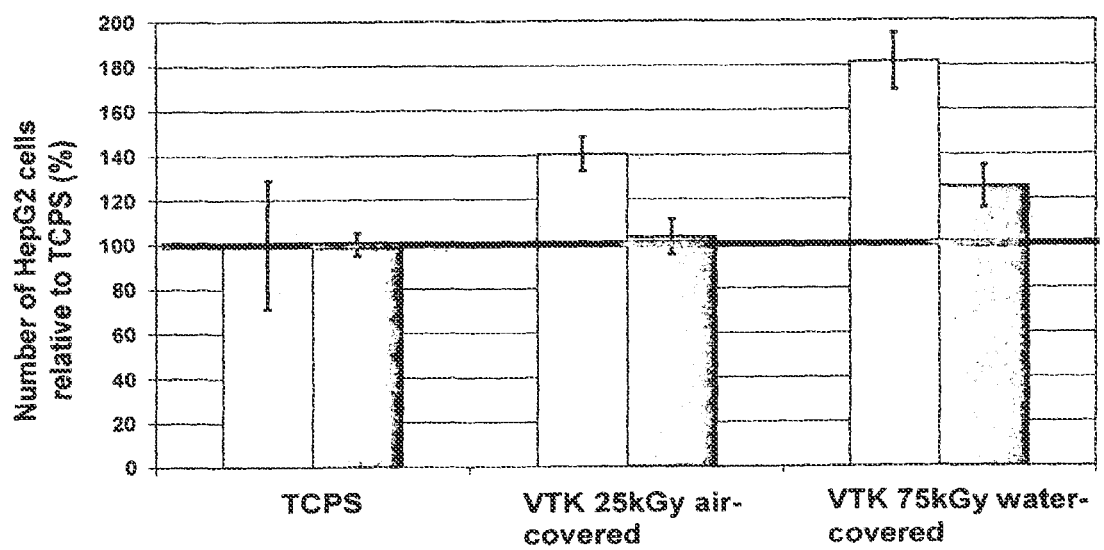
FIG. 11 shows the results of a short-term cell culture of human hepatocarcinoma cells (HepG2) on VTK membranes irradiated with 25 kGy (air-covered) or 75 kGy (water-covered) in comparison with TCPS. Left columns show the number of HepG2 cells after 1 day relative to the number of cells on TCPS, i.e. they depict the efficiency of cell adhesion. Right columns show the number of HepG2 cells after 5 days relative to the number of cells on TCPS, i.e. they depict the efficiency of cell proliferation. The membranes according to the invention show a cell adhesion and proliferation which is superior to a TCPS surface.
Figure 12:
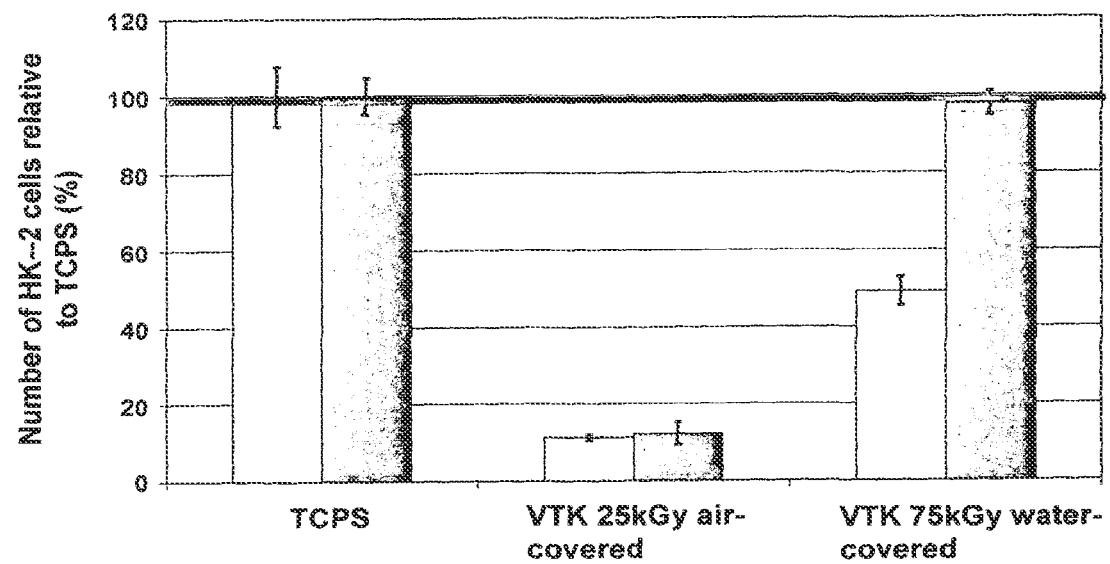
FIG. 12 shows the results of a short-term cell culture of human renal epithelial cells (HK-2) on VTK membranes irradiated with 25 kGy (air-covered) or 75 kGy (water-covered) in comparison with TCPS. Left columns show the number of HK-2 cells after 1 day relative to the number of cells on TCPS, i.e. they depict the efficiency of cell adhesion. Right columns show the number of HK-2 cells after 5 days relative to the number of cells on TCPS, i.e. they depict the efficiency of cell proliferation.
Figure 13:
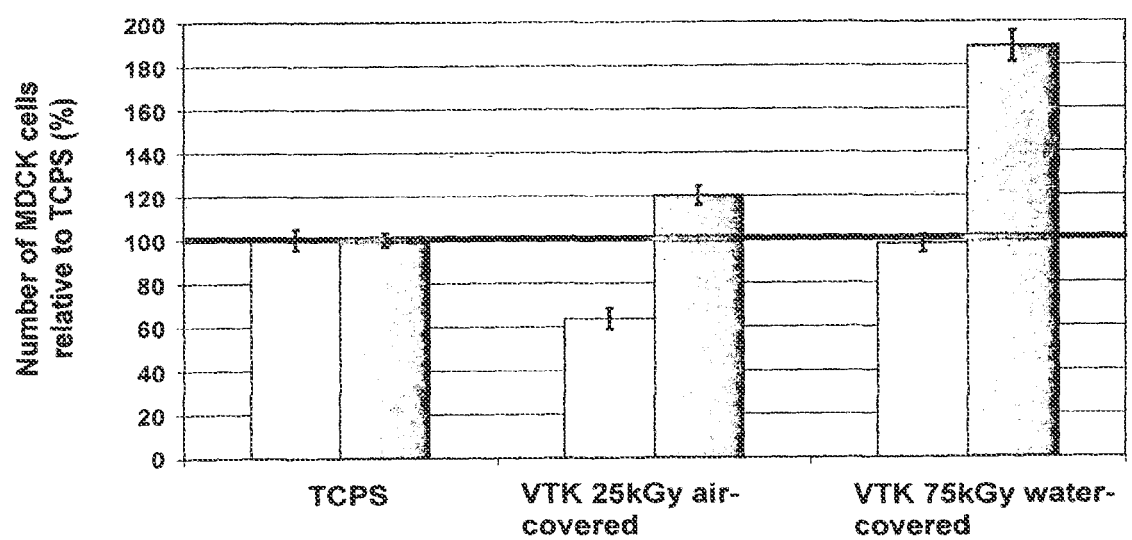
FIG. 13 shows the results of a short-term cell culture of canine renal epithelial cells (MDCK) on VTK membranes irradiated with 25 kGy (air-covered) or 75 kGy (water-covered) in comparison with TCPS. Left columns show the number of MDCK cells after 1 day relative to the number of cells on TCPS, i.e. they depict the efficiency of cell adhesion. Right columns show the number of MDCK cells after 5 days relative to the number of cells on TCPS, i.e. they depict the efficiency of cell proliferation.

MSC were seeded into 24-well plates at a density of approx. 10,000 MSC/cm$^2$. Three wells were used, one to differentiate MSC into osteoblasts as described below, one well to grow MSC in standard MSC expansion medium (without inducing osteogenesis) and one as control for stainings. MSC were grown to confluency or up to ten days over confluency using standard MSC medium. The MSC medium was replaced with the osteogenic differentiation media (100 µl glycerol phosphate stock solution (2.16 g glycerol phosphate in 100 ml of standard MSC medium), 1 µl dexamethasone stock solution, and 1 µl ascorbic acid stock solution (0.145 g ascorbic acid in 10 ml of basal medium, alpha-MEM), in 1 m standard MSC medium) and changed every 3-4 days. After 2-3 weeks, there were calcified deposits in and around the cells. Cells were washed in PBS. PBS was removed and the cells were fixed with 10% formaldehyde for 10 min, followed by washing once with PBS and twice with deionized water. Cells were air-dries and stained with silver nitrate under UV light for 10 min. After washing 2-3 times with deionized water, cells were counterstained with Mayer's Hematoxylin, followed by washing in tap water for one minute, then by washing twice with deionized water. Cells were embedded in 10% formaldehyde. FIG. 9 depicts the successful osteogenesis of cells which were grown on membranes according to the invention.

Example 13

Suitability for Expansion of Various Cell Types

In order to assess the applicability of the gamma-irradiated membranes according to the invention for the cultivation of various cell types, flat membranes were exemplarily tested. The membranes used were as described in Examples 10 and 11 and referred to as "VTK" membranes. The membranes were irradiated with 25 (air-covered) and 75 kGy (water-covered), respectively. The membranes were tested in short-term culture, thereby assessing cell adhesion (1 day after seeding) and cell proliferation (5 days after reseeding) in comparison to standard TCPS. The cells used were (a) NHDF, normal human dermal fibroblasts, (b) HepG2, a human hepatocarcinoma cell line, (c) HK-2, a human renal proximal epithelial cell line, and (d) MDCK, the Madin-Darby canine kidney epithelial cell line. The cells (a) through (d) were tested on the membranes according to the invention and on TCPS. The cells were seeded as follows: (a) NHDF: $5 \cdot 10^3$ cells/cm$^2$ in medium (DMEM+10 FBS+1% penicillin/streptomycin); (b) HepG2: 5.6×10a cells/cm$^2$ in medium (RPMI+10% FBS+0.5% Gentamycine); (c) HK-2: $10^4$ cells/cm$^2$ in medium (Keratinocyte SFM (Gibco, Cat #17005)+Supplements for Keratinocyte SFM (Gibco, Cat #37000-015)+10 µg/ml Meronem+1% FBS+1% CaCl$_2$); (d) MDCK: $10^o$ cells/cm$^2$ in medium (M199+10 µg/ml Meronem+10% FBS (heat inactivated)). Cell numbers were determined 1 day (adhesion) and 5 days (proliferation) after cell seeding by CASY counting. FIGS. 10 through 13 show that all cell types could be efficiently expanded on 75 kGy irradiated membranes. The results prove that the membranes are at least as efficient as standard TCPS, especially with regard to cell expansion. The results are show that membranes which have been treated with higher doses are slightly better suited for cell cultivation than membranes having been treated with a lower dose. The membrane VTK 25 kGy, did not work out efficiently with HK-2 cells (FIG. 12), probably due to problems in the first removal of the cells after the first day.

Example 14

MSC Expansion on Gamma-Ray Irradiated Hollow Fiber Membranes (Bioreactors) from Unprocessed Bone Marrow The expansion of MSC from unprocessed bone marrow and the expansion of pre-selected MSC were done in various hollow fiber bioreactors in a Cell Expansion System (CES). Bioreactors which proved to be suitable for pre-selected MSC were further tested with unprocessed bone marrow. The doubling times in bioreactors according to the invention were compared to doubling times in control flasks (TCPS) starting from the same cell density at seeding. The doubling time served as a method to assess the performance of the various membranes/TCPS.

Pre-selected MSC: MSC used were pre-selected, cryopreserved MSC from bone marrow at maximum passage four. MSC were pre-selected by expansion of bone marrow-derived MSC in conventional TCPS flasks for at least two passages. Approximately 2.8 Mio MSC were loaded in a 1.7 m² bioreactor which corresponds to 164 MSC/cm². In case the surface area was smaller than 1.7 m² the number of loaded MSC was scaled. The culture period was 7 days.

Unprocessed bone-marrow: Approximately 10-12 ml of bone marrow was loaded in a 1.7 m² bioreactor, in case the surface area was less than 1.7 in, the volume of loaded bone marrow was scaled. The culture period was 13 days.

T75 TCPS flasks served as control flasks. Pre-selected MSC were seeded in flasks in the same density as in bioreactors (164 MSC/cm²). When starting with unprocessed bone marrow, 234 µl bone marrow were seeded in flasks (3.12 µl/cm²) and 12 ml bone marrow was loaded into 1.7 m² bioreactors (0.71 µl/cm²).

The membrane types used in this experiment are summarized in Table III. Membranes based on PES/PVP/PA were prepared as described in Example 3. Membranes based on PES/PVP/PU were prepared as described in Example 5. The expression PAN refers to polyacrylonitrile.

TABLE III

Overview of membrane types which were tested with regard to the expansion of pre-selected MSC and unprocessed bone marrow.

| No. | Type | Treatment | Membrane material |
|---|---|---|---|
| 1 | VTK coated with fibronectin | steam | PES/PVP/PA |
| 2 | AN69ST (surface treated) | gamma-irradiation | PAN/PEI |
| 3 | AN69XS (not surface treated) | gamma-irradiation | PAN |
| 4 | 0.5% PU (not online-dried) | gamma-irradiation | PES/PVP/PU |
| 5 | VTK air-filled 25 kGy | gamma-irradiation | PES/PVP/PA |
| 6 | VTK air-filled 75 kGy | gamma-irradiation | PES/PVP/PA |
| 7 | VTK water-filled 25 kGy | gamma-irradiation | PES/PVP/PA |
| 8 | VTK water-filled 75 kGy | gamma-irradiation | PES/PVP/PA |
| 9 | VTK AA 0.001% 25 kGy | gamma-irradiation | PES/PVP/PA/(AA) |
| 10 | VTK AA 0.001% 75 kGy | gamma-irradiation | PES/PVP/PA/(AA) |
| 11 | VTK AA 0.01% 25 kGy | gamma-irradiation | PES/PVP/PA/(AA) |
| 12 | VTK AA 0.01% 75 kGy | gamma-irradiation | PES/PVP/PA/(AA) |

The results for the membranes were compared to standard TCPS flasks. A membrane which was not gamma-ray irradiated but instead coated with fibronectin (1) was included in this experiment for reasons of comparison.

The bone marrow was seeded on day 0 into the bioreactors and the flasks. On day 2 the medium was exchanged for the first time and then again on days 4 or 5, 6 or 7, 8 to 10 and 10 to 12. On day 13 the cells were harvested (trypsin) and the cells were counted. The viability of the cells was tested as well as their phenotype and morphology and/or their proliferation behavior.

Counting of Cell Colonies for the Calculation of Starting Cell Number when Using Unprocessed Bone Marrow (CFU-F)

78 µl unprocessed bone marrow was seeded into T25 (TCPS) flasks containing 5 ml MSC medium. The non-adherent cells were removed after 2 to 3 days by washing twice with PBS, followed by adding fresh MSC medium. The MSC medium was exchanged every 2 to 3 days. On day 7 the colonies were counted (10-fold magnification/microscope).

Calculation of Doubling Time and Doubling Time Ratio

Doubling time (DT) is the period of time required for a cell to double in number. DT of MSC and DT ratio were calculated as follows.

$$\text{Number of } MSC \text{ doubling} = \log_2\left(\frac{N}{N_0}\right).$$

N is the number of MSC obtained after the indicated culture period, $N_0$ is the number of seeded MSC.

DT (hours)=Culture period (hours)/Number of doublings.

The DT ratio=DT of cells in bioreactor/DT of cells in control flasks.

Figure 14:
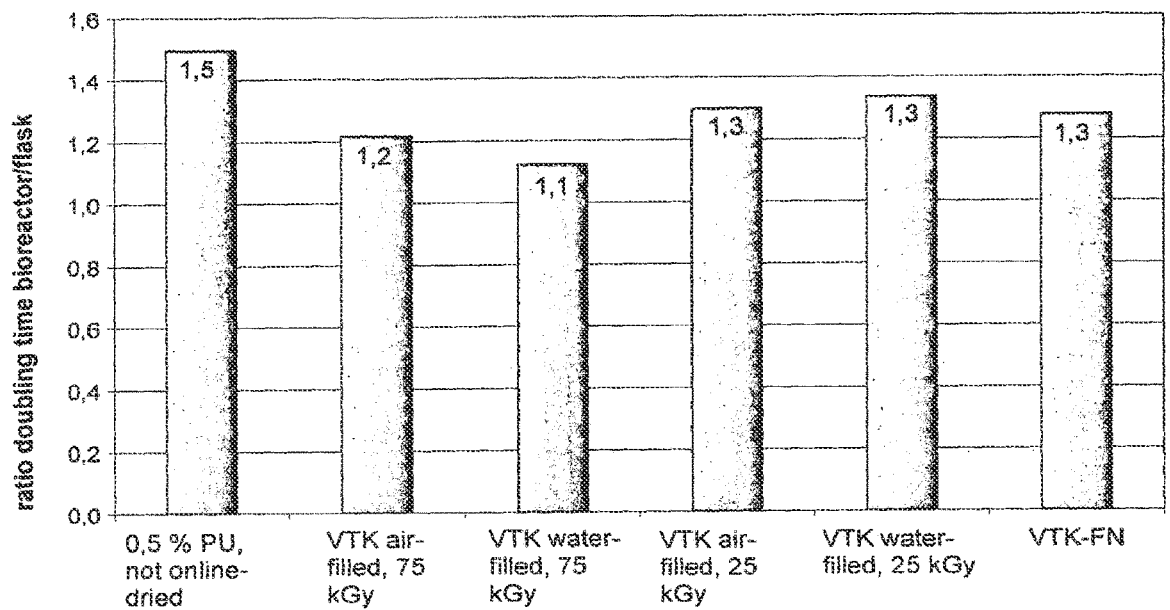
FIG. 14 shows the doubling time ratio of cells in bioreactors based on membranes according to the invention compared to the standard flask culture (see Example 15). The doubling time refers to the doubling time of cells in a given bioreactor/doubling time of cells in control flasks.

All selected gamma-irradiated bioreactors with unprocessed bone marrow showed performance comparable to TCPS and VTK-FN bioreactors. Doubling times ranged from 28 to 34 hours which was only slightly higher than in the control flasks (23 to 25 hours). Therefore, the doubling time ratio ranged from 1.1 to 1.5 (FIG. 14). The 0.5% PU bioreactor showed slightly slower cell growth compared to gamma-irradiated bioreactors and the VTK-FN bioreactor.

Figure 15:
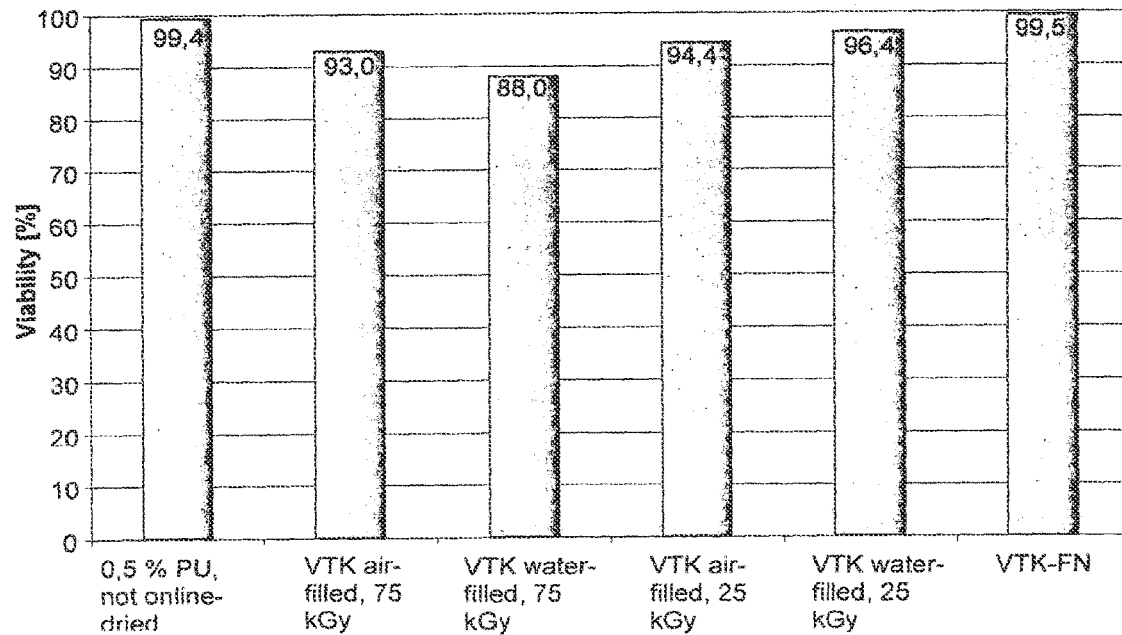
FIG. 15 shows the viability of MSC which were cultivated from unprocessed bone marrow. The viability of harvested cells was above 90% for all bioreactors tested.

Viability of harvested cells (FIG. 15) was tested by FACS analysis with 50,000 cells per FACS tube in MSC medium. One sample was stained with propidium iodide solution (end conc. 1 µg/ml) for 10 to 15 minutes at room temperature in the dark. Another unstained sample was used as reference. Viability of the harvested cells ranged from 88 to 99.5%.

Figure 16:
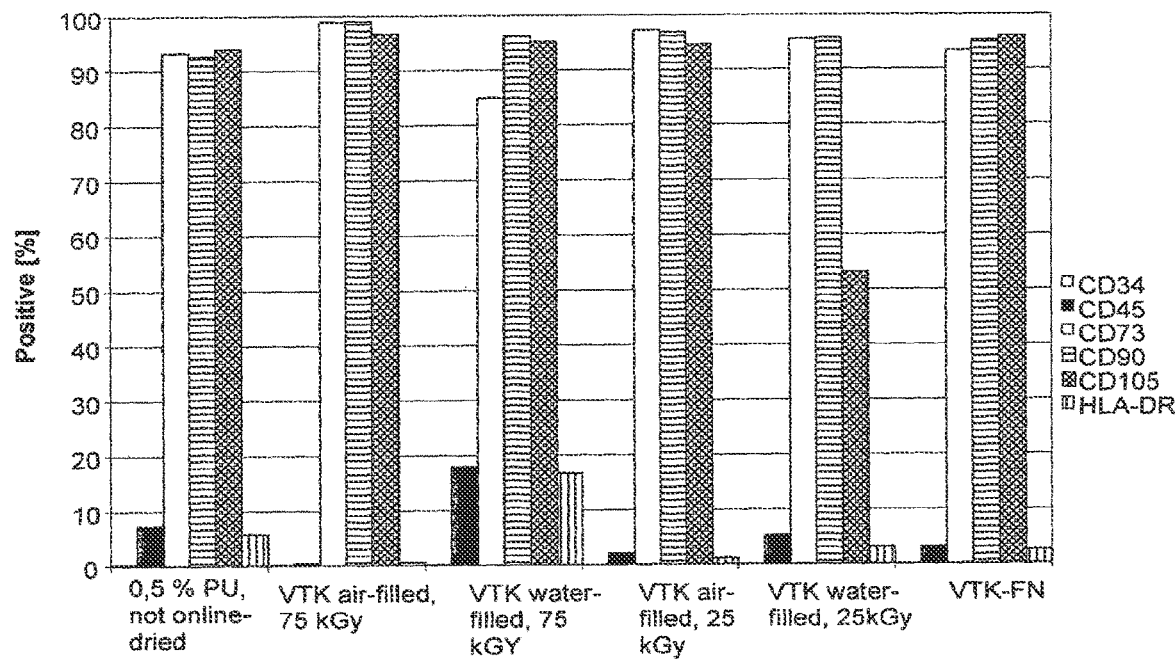
FIG. 16 shows the phenotype of cells harvested from bioreactors according to the invention. The MSC were cultivated from unprocessed bone marrow. As can be seen, the cells expanded in the VTK water-filled bioreactor (75 kGy) showed comparatively high values for CD45 and HLA-DR. The Cells harvested from all other bioreactors showed the expected Phenotype of MSC with regard to CD34, CD45, CD73, CD90, CD105 and HLA-DR.

Phenotype of harvested cells (see FIG. 16) was tested after trypsinization of cells. 1 million cells were resuspended in 5,000 µl blocking buffer (cell wash+10% human serum) and incubated at 4° C. for 30 minutes. 50 µl each were distributed into 10 tubes, and antibodies were added (one unstained (no antibody): CD34-PE—2 µl, CD45-PE—2 µl, CD73-PE—2 µl, mIgG1-PE—1 µl (isotype control for CD34, CD45, CD73), HLA-DR,DP,DQ-FITC—2 µl, mIgG2a-FITC—1 µl (isotype control for HLA-DR), CD90-FITC—1 µl, CD105-FITC—1 µl, mIgG1-FITC—2 µl (isotype control for CD90, CD105). The mixtures were mixed well and stored in the dark at room temperature for 20 minutes. Then 1 ml FACS buffer was added (cell wash+2% FBS (heat inactivated)) and vortexed, followed by centrifugation for 3 minutes at 400 g. The buffer was removed and the pellet was vortexed. Then 400 µl fixation buffer (diluted 1:10 with water) was added and vortexed. The cells were stored at 4° C. and analyzed within 4 days.

Cells expanded in the gamma-modified, water-filled bioreactor irradiated with 75 kGy showed comparatively high values for CD45 and HLA-DR (18 and 16.7% of cells were positive, respectively). Cells harvested from all other bioreactors showed the expected phenotype of MSC.

Examination of re-attachment on TCPS post expansion showed mostly spindle-shaped cells which exhibited a normal growth behavior post re-plating (data not shown).

Example 15

Influence of Radiation Dose

Figure 17:
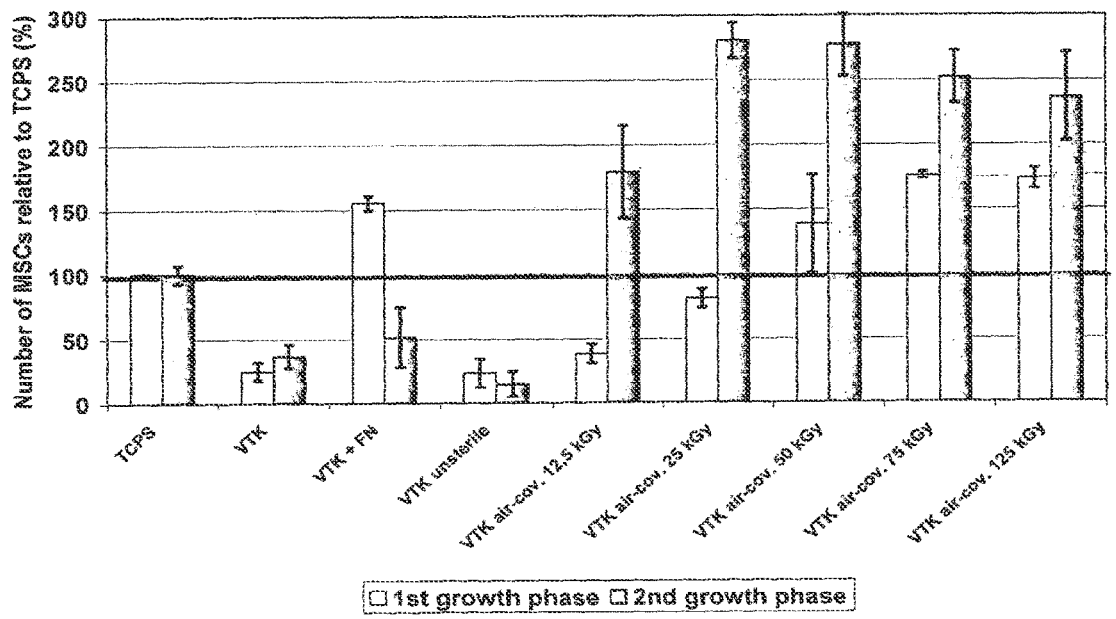
FIG. 17 shows the number of MSC grown from pre-selected MSC on various membrane types relative to the number of MSC Grown on standard TCPS after the first (10 days) and second (11 days) growth phase in [%]. The results indicate the effects of the gamma-ray dose on the cell proliferation properties of the membranes. The horizontal line indicates TCPS level.

To investigate the influence of the radiation dose on the membrane properties, Example 14 was repeated with pre-selected MSC using VTK membranes irradiated air-filled with gamma-ray radiation doses between 12.5 kGy and 125 kGy, and the number of MSC grown relative to the number of MSC grown on standard TCPS after the first (10 days) and second (11 days) growth phase was determined. The results are shown in FIG. 17.

The invention claimed is:

1. A method for the cultivation of adherent cells, the method comprising the steps of:
preparing a membrane comprising i) a component selected from the group consisting of a polysulfone, polyethersulfone, a polyarylethersulfone, and combinations thereof, and ii) a polyvinylpyrrolidone,
irradiating the prepared membrane with at least one of gamma-rays, beta-rays, and an electron beam in a dose of from 12.5 to 175 kGy in the presence of oxygen at a concentration of 4 to 100 vol %, and
inoculating the irradiated membrane with the adherent cells to be cultivated.

2. The method according to claim 1, wherein the adherent cells are selected from the group consisting of stem cells, embryonic stem cells, adult stem cells, mesenchymal stem cells (MSC), hematopoietic stem cells, cord blood cells, neural stem cells, smooth muscle cells, skin cells, nerve cells, neuroglia cells, endothelial cells, epithelial cells, fibroblasts, hepatocytes, endothelial cells, muscle cells, and chondrocytes.

3. The method according to claim 1, wherein the adherent cells are mesenchymal stem cells.

4. The method according to claim 1, wherein the adherent cells are liver cells.

5. The method according to claim 1, wherein the adherent cells are renal cells.

6. The method according to claim 1, wherein the adherent cells are epithelial cells.

7. The method according to claim 1, wherein the adherent cells are fibroblasts.

8. The method according to claim 1, wherein irradiating the prepared membrane is in a dose of from 70 to 175 kGy.

9. The method according to claim 1, wherein irradiating the prepared membrane is with gamma-rays, beta-rays, or a combination of both.

10. The method according to claim 1, wherein the irradiating is in the presence of oxygen at a concentration of 4 to 30 vol %.

11. A method for the extracorporeal treatment of body fluids, the method comprising the steps of:
preparing a membrane comprising i) at least one of a polysulfone, a polyethersulfone, and a polyarylethersulfone, and ii) a polyvinylpyrrolidone,
irradiating the prepared membrane with at least one of gamma-rays, beta-rays, and an electron beam in a dose of from 12.5 to 175 kGy in the presence of oxygen at a concentration of 4 to 100 vol %, and
inoculating the irradiated membrane with adherent cells for treating the body fluid.

12. The method according to claim 11, wherein the adherent cells are selected from the group consisting of stem cells, embryonic stem cells, adult stem cells, mesenchymal stem cells (MSC), hematopoietic stem cells, cord blood cells, neural stem cells, smooth muscle cells, skin cells, nerve cells, neuroglia cells, endothelial cells, epithelial cells, fibroblasts, hepatocytes, endothelial cells, muscle cells, and chondrocytes.

13. The method according to claim 11, wherein the adherent cells are mesenchymal stem cells.

14. The method according to claim 11, wherein the adherent cells are liver cells.

15. The method according to claim 11, wherein the adherent cells are renal cells.

16. The method according to claim 11, wherein the adherent cells are epithelial cells.

17. The method according to claim 11, wherein the adherent cells are fibroblasts.

18. The method according to claim 11, wherein irradiating the prepared membrane is in a dose of from 70 to 175 kGy.

19. The method according to claim 11, wherein irradiating the prepared membrane is with gamma-rays, beta-rays, or a combination of both.

20. The method according to claim 11, wherein the irradiating is in the presence of oxygen at a concentration of 4 to 30 vol %.

* * * * *